US007132650B1

(12) United States Patent
Gamble et al.

(10) Patent No.: US 7,132,650 B1
(45) Date of Patent: Nov. 7, 2006

(54) HIGH THROUGHPUT MULTI-DIMENSIONAL SAMPLE ANALYSIS

(75) Inventors: Ronald C. Gamble, Altadena, CA (US); Stephen D. O'Connor, Pasadena, CA (US); Bruce Wilcox, Lake Elsinore, CA (US); Matthew M. Gregori, Pasadena, CA (US)

(73) Assignee: Nanostream, Inc., Pasadena, CA (US)

( * ) Notice: Subject to any disclaimer, the term of this patent is extended or adjusted under 35 U.S.C. 154(b) by 220 days.

(21) Appl. No.: 10/951,255

(22) Filed: Sep. 25, 2004

Related U.S. Application Data

(60) Provisional application No. 60/506,452, filed on Sep. 26, 2003.

(51) Int. Cl.
*H01J 49/42* (2006.01)

(52) U.S. Cl. ............ 250/288; 137/625.46; 137/625.47; 73/864.83; 73/23.42; 436/50

(58) Field of Classification Search ...................... None
See application file for complete search history.

(56) References Cited

U.S. PATENT DOCUMENTS

| | | | |
|---|---|---|---|
| 5,872,010 A | 2/1999 | Karger et al. | 436/173 |
| 6,066,848 A | 5/2000 | Kassel et al. | 250/288 |
| 6,436,292 B1 | 8/2002 | Petro | 210/656 |
| 6,465,776 B1 | 10/2002 | Moini et al. | 250/285 |
| 6,508,938 B1 | 1/2003 | Maiefski et al. | 210/659 |
| 6,541,768 B1 | 4/2003 | Andrien, Jr. et al. | 250/288 |
| 6,621,075 B1 | 9/2003 | Hindsgaul et al. | 250/288 |
| 6,632,404 B1 | 10/2003 | Freitag et al. | 422/103 |
| 6,641,783 B1 | 11/2003 | Pidgeon et al. | 422/70 |
| 6,649,908 B1 | 11/2003 | Apffel, Jr. et al. | 250/288 |
| 6,812,030 B1 | 11/2004 | Ozbal et al. | 436/50 |
| 6,910,503 B1 * | 6/2005 | Schick et al. | 137/625.47 |
| 2002/0068366 A1 | 6/2002 | LaDine et al. | 436/518 |
| 2003/0136904 A1 | 7/2003 | Mukaibatake | 250/288 |
| 2004/0134546 A1 | 7/2004 | Schick et al. | 137/625.46 |

FOREIGN PATENT DOCUMENTS

WO     WO 02/44684 A2     6/2002

OTHER PUBLICATIONS

Misharin, Alexander S. et al., *High-Throughput Mass Spectrometer Using Atmospheric Pressure Ionization and a Cylindrical Ion Trap Array*, "Analytical Chemistry," vol. 77, No. 2, Jan. 15, 2005, pp. 459-470.

\* cited by examiner

*Primary Examiner*—Nikita Wells
*Assistant Examiner*—Zia R. Hashmi
(74) *Attorney, Agent, or Firm*—Vincent K. Gustafson; Intellectual Property/Technology Law

(57) ABSTRACT

High throughput analytical systems and methods employing multiple liquid phase separation process regions coupled to a common mass spectrometer are provided. Disclosed systems and methods permits parallel separation and parallel storage of discrete eluate fractions, followed by sequential discharge and ionization of previously stored eluate portions to yield a composite ion stream containing the sequential series of eluate portions, followed by mass analysis of the ion stream. A common manifold may receive ions and utilize pressurized gas or ion gating to direct ions within the manifold toward the mass spectrometer inlet.

65 Claims, 18 Drawing Sheets

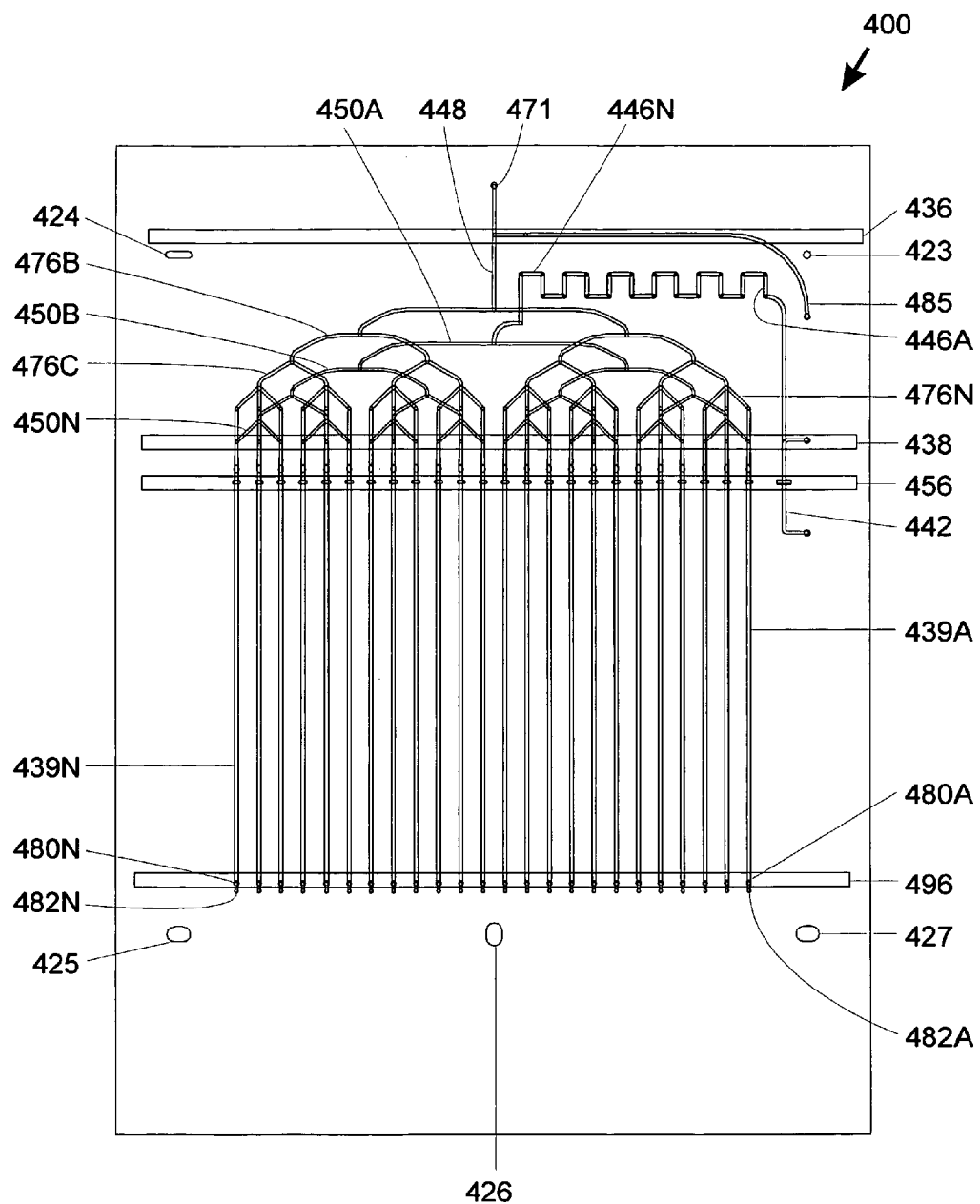
FIG._1

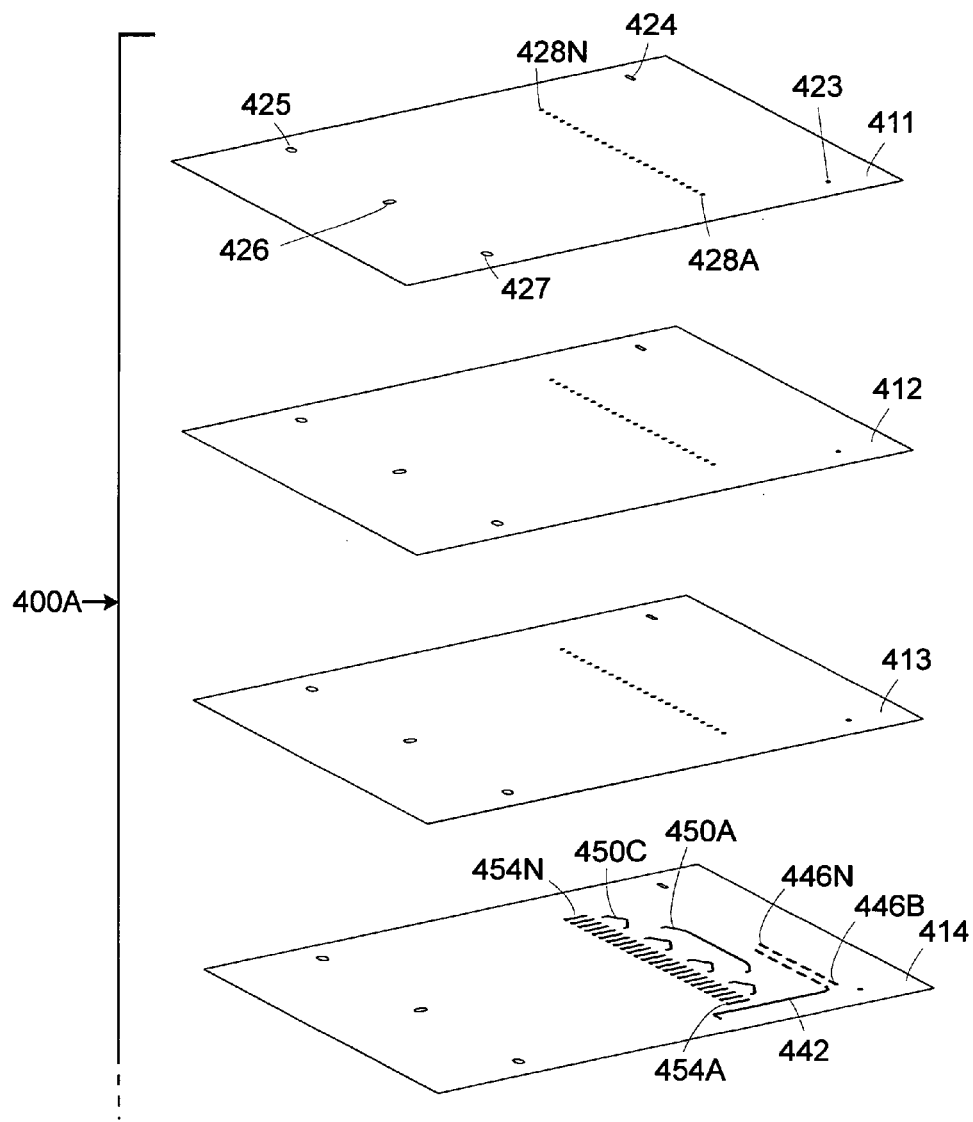
FIG._2A

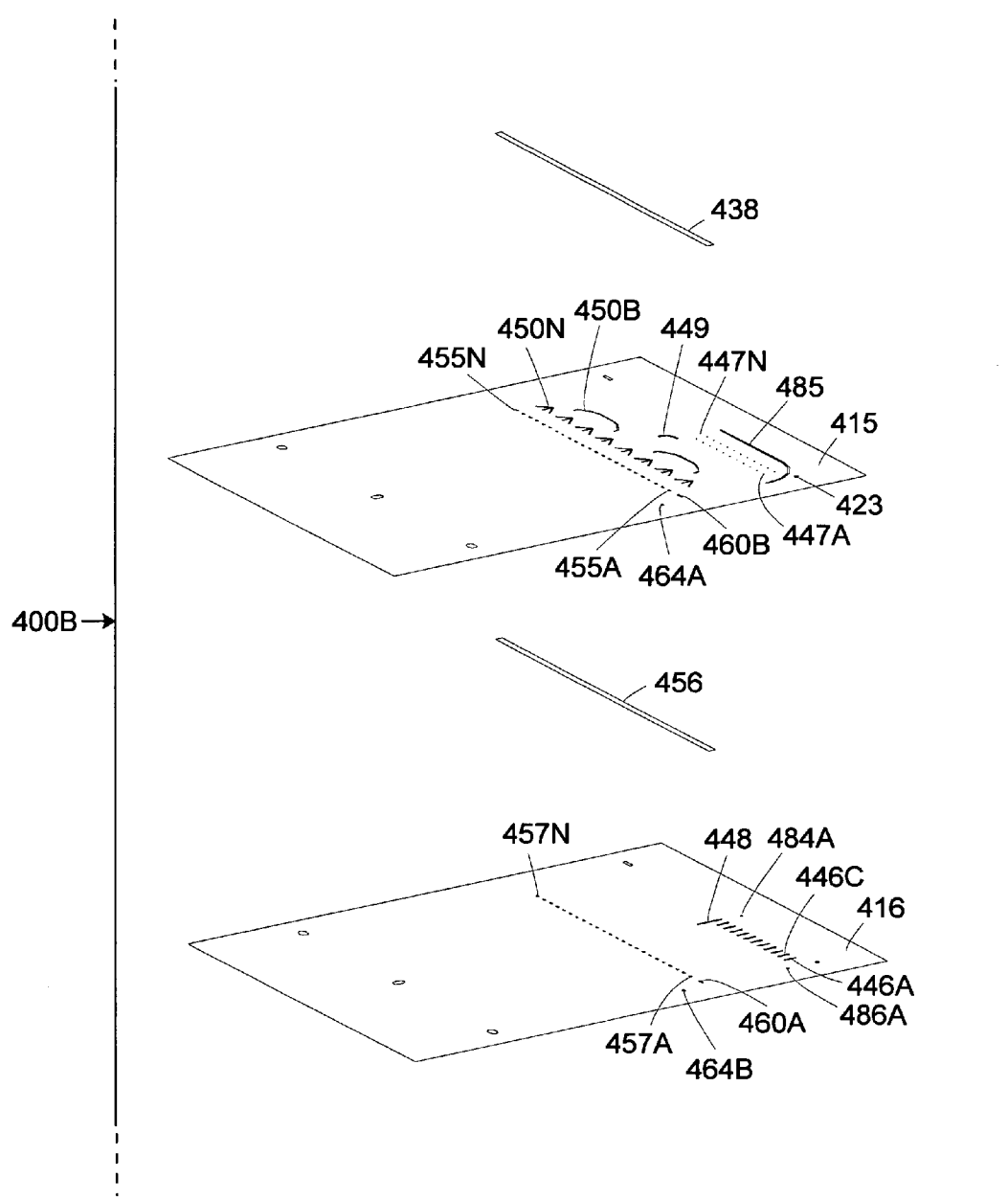
FIG._2B

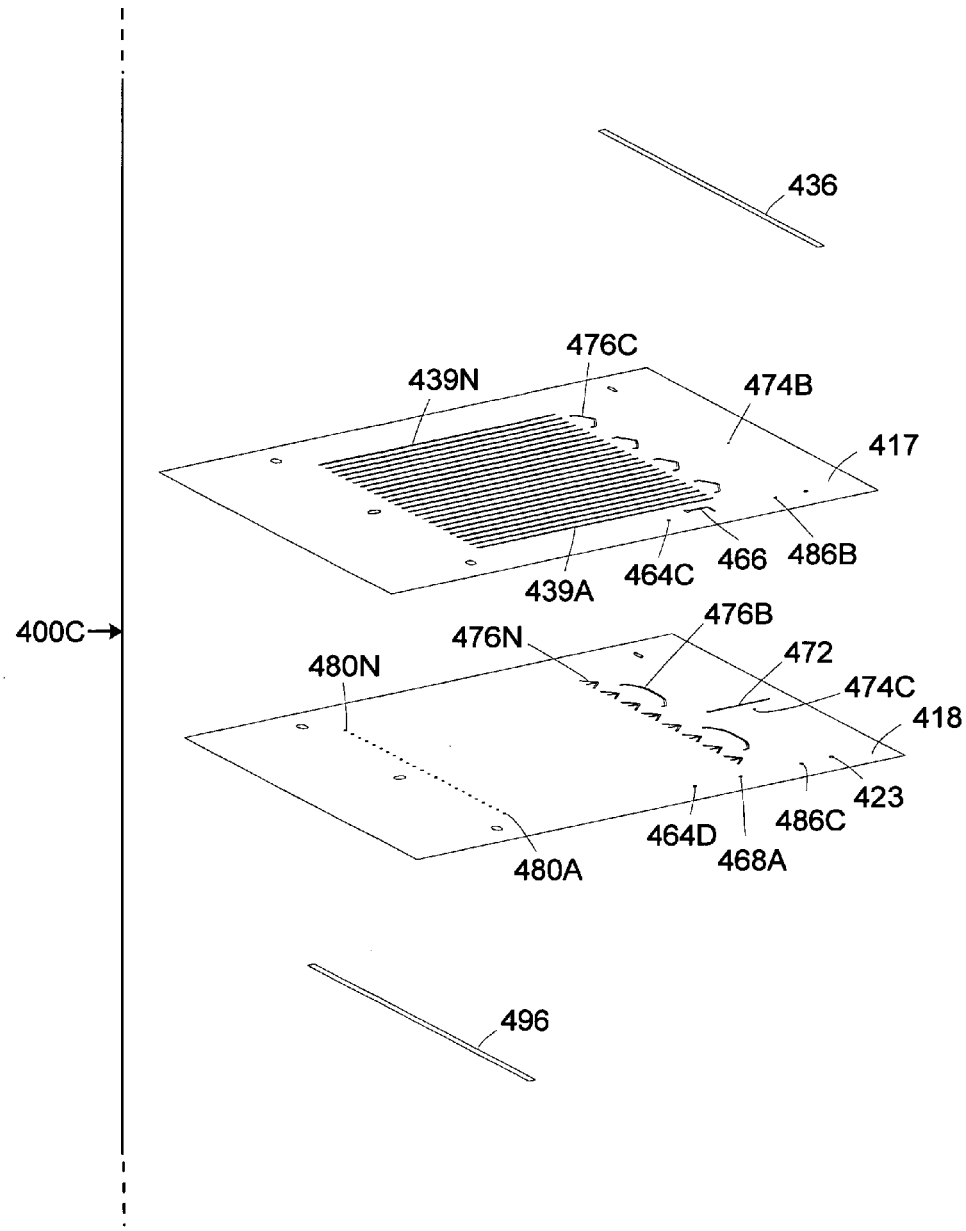
FIG._2C

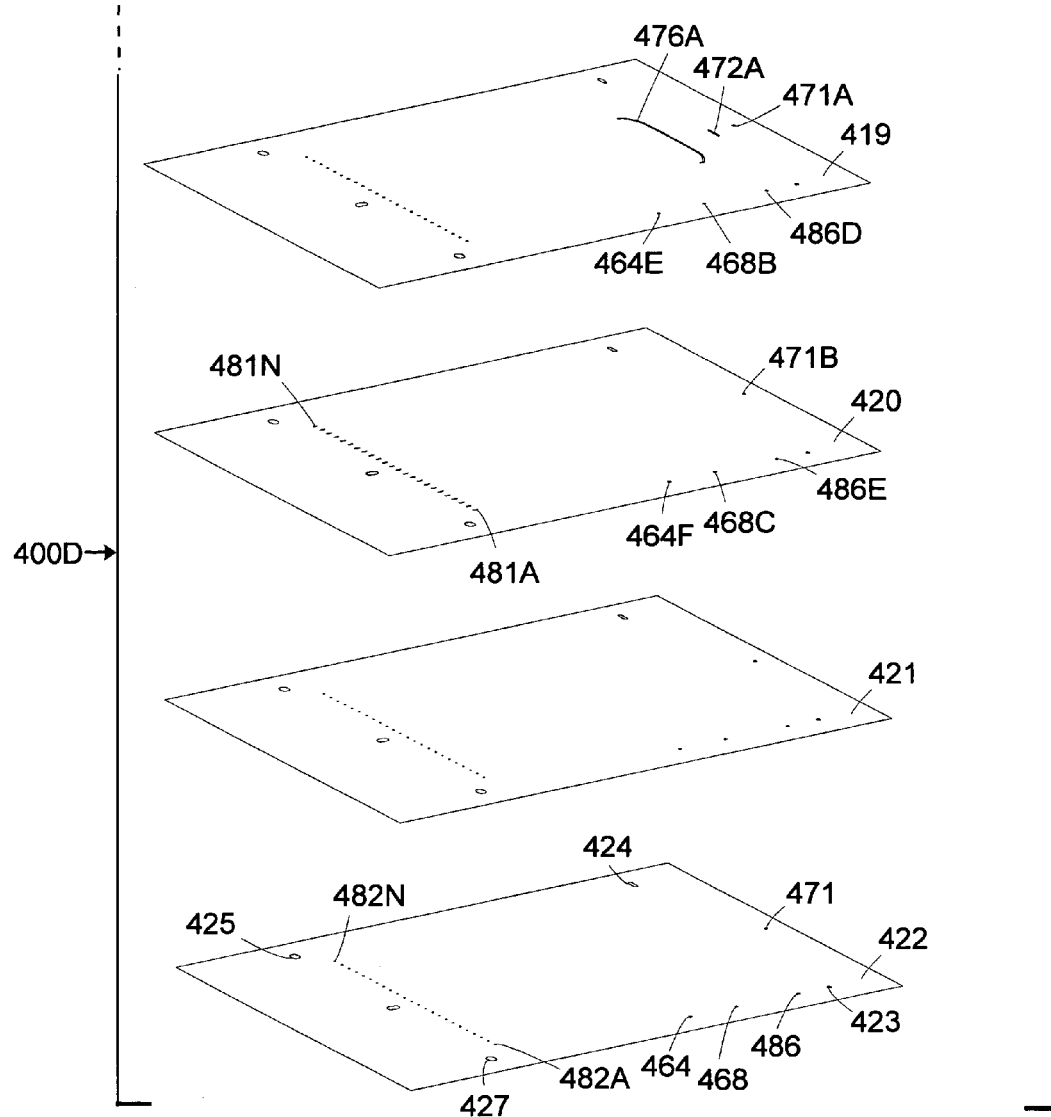
FIG._2D

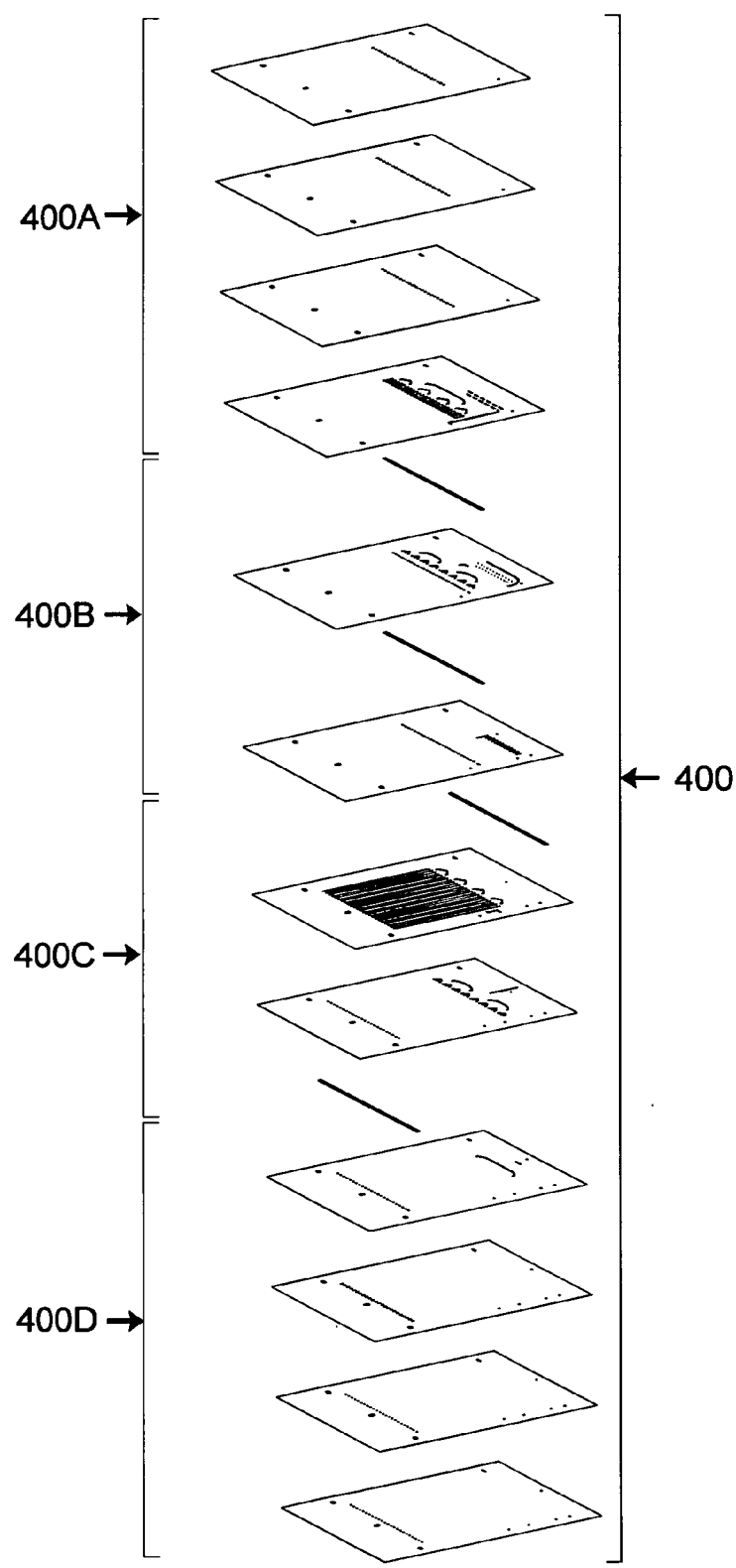
FIG._2E

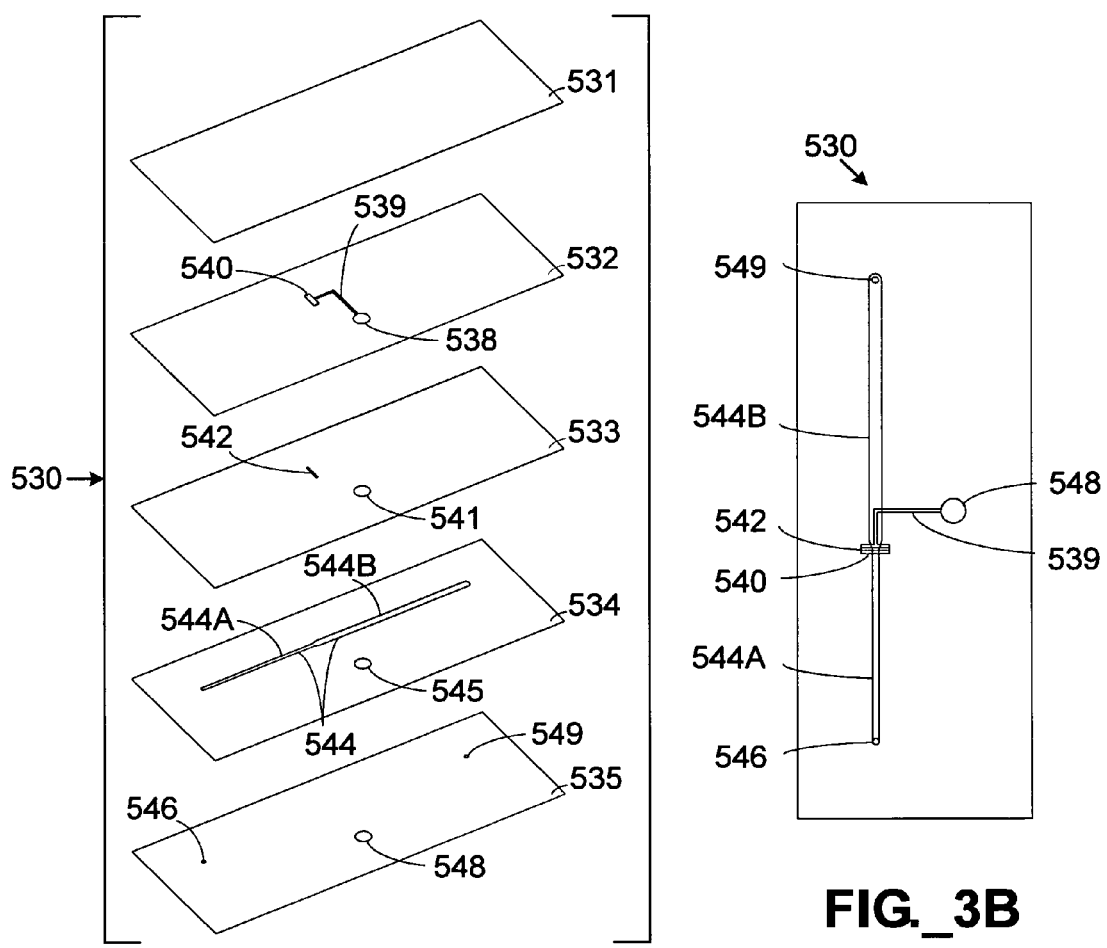
FIG._3A
FIG._3B

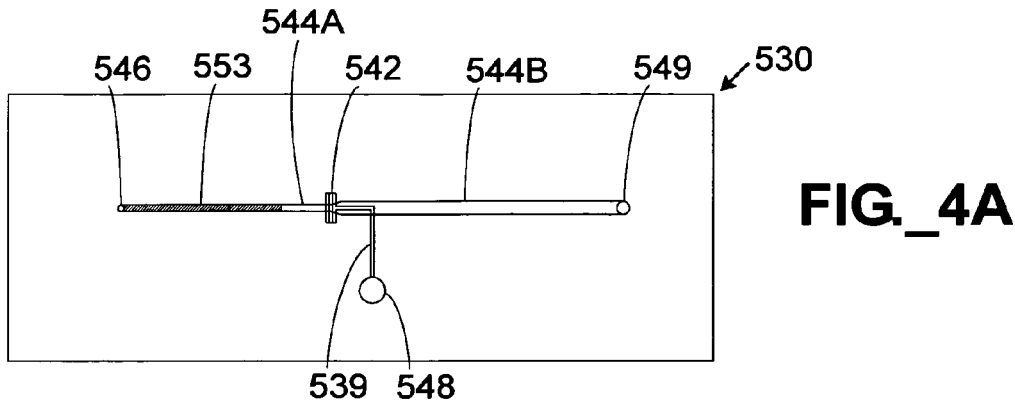
FIG._4A
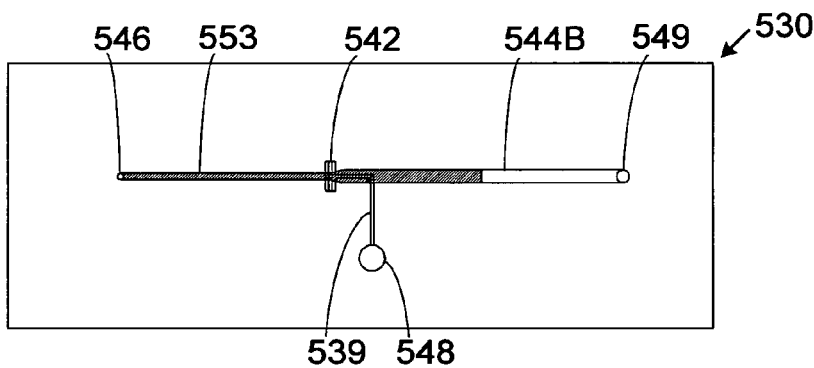
FIG._4B
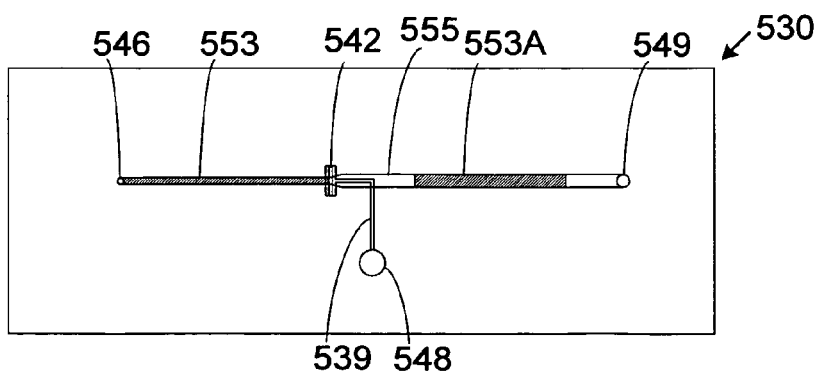
FIG._4C

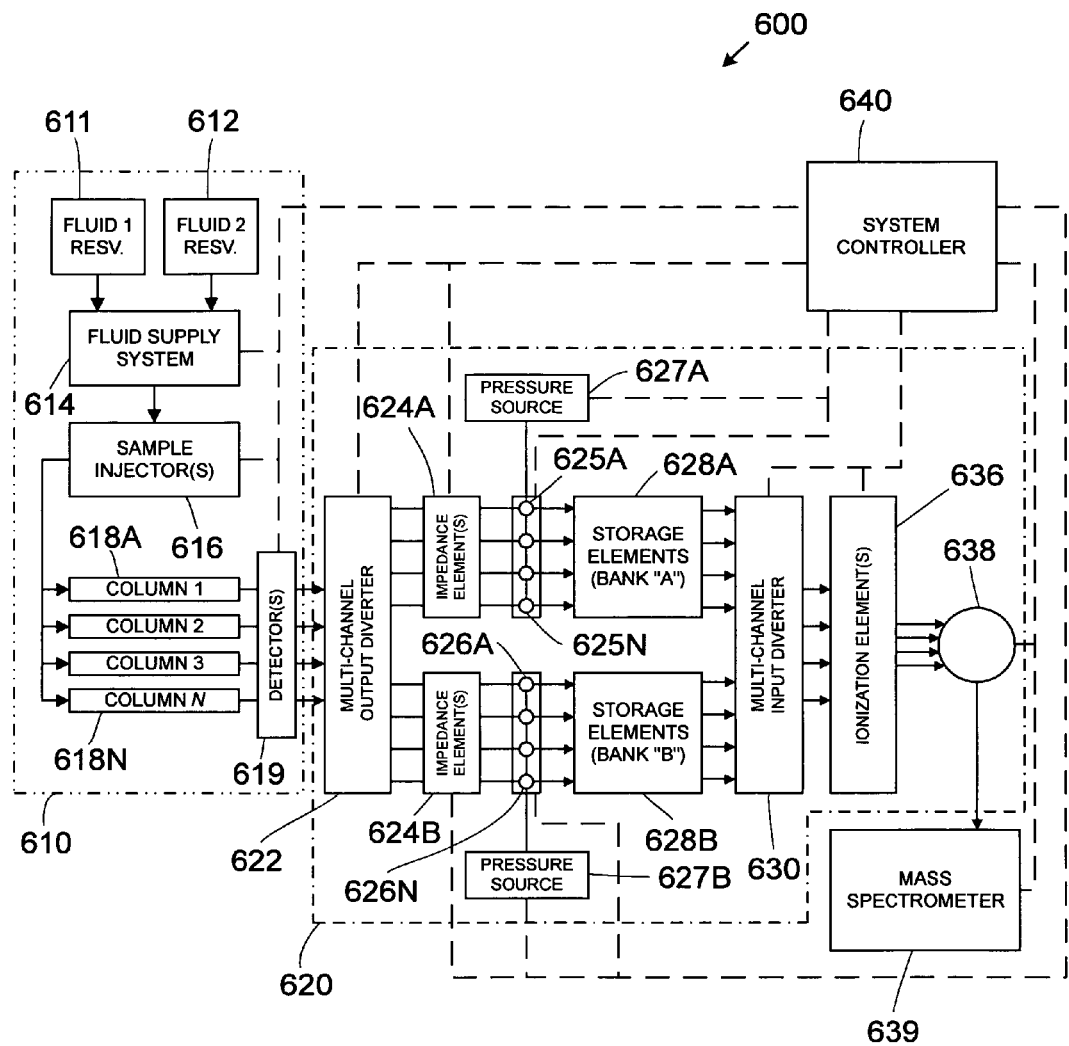
FIG._5

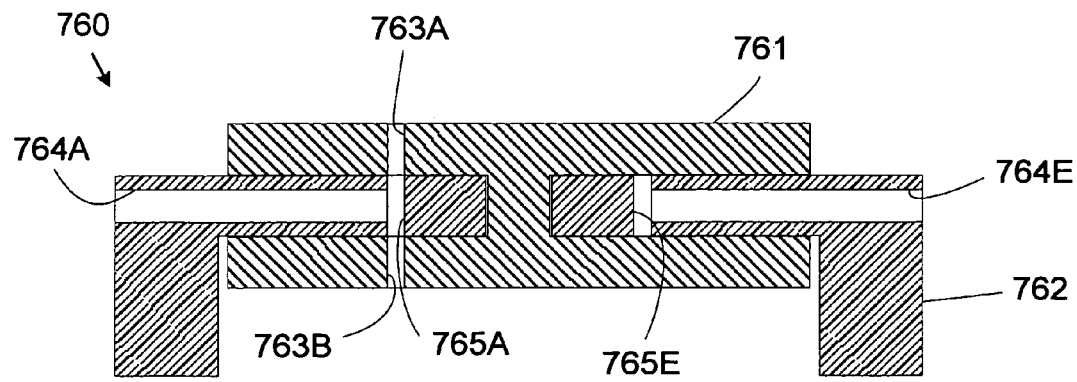
FIG._7A
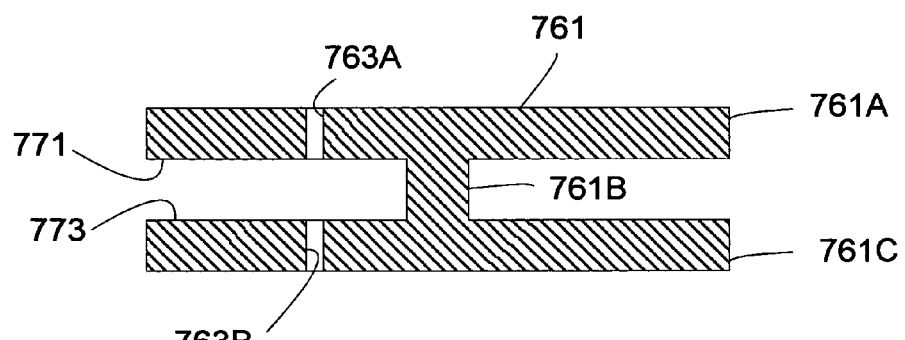
FIG._7B
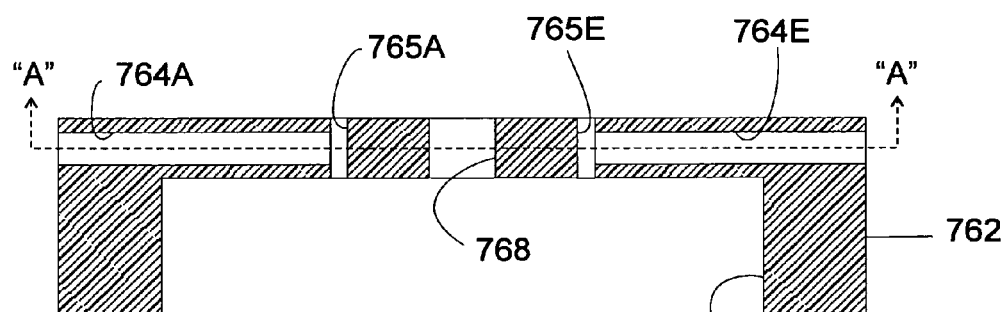
FIG._7C

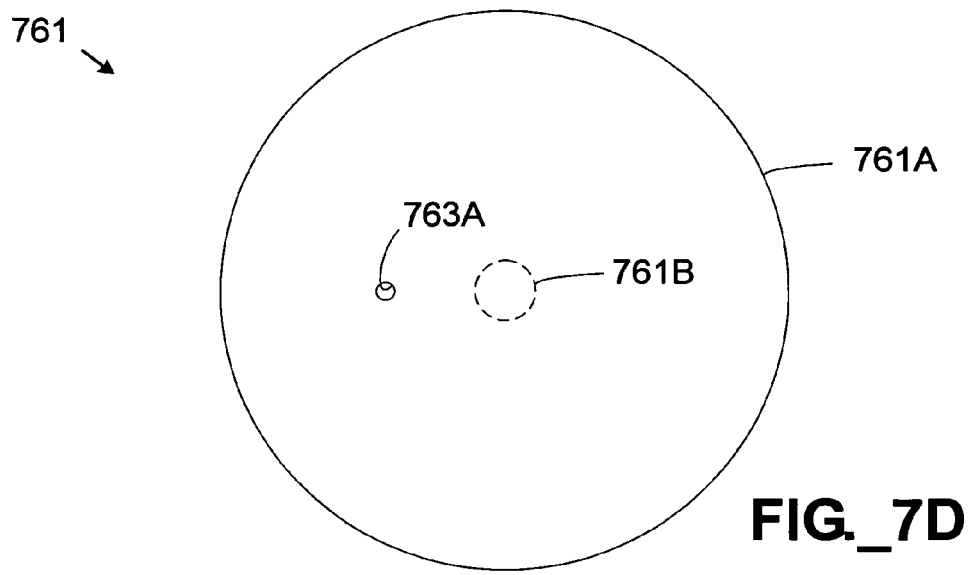
FIG._7D
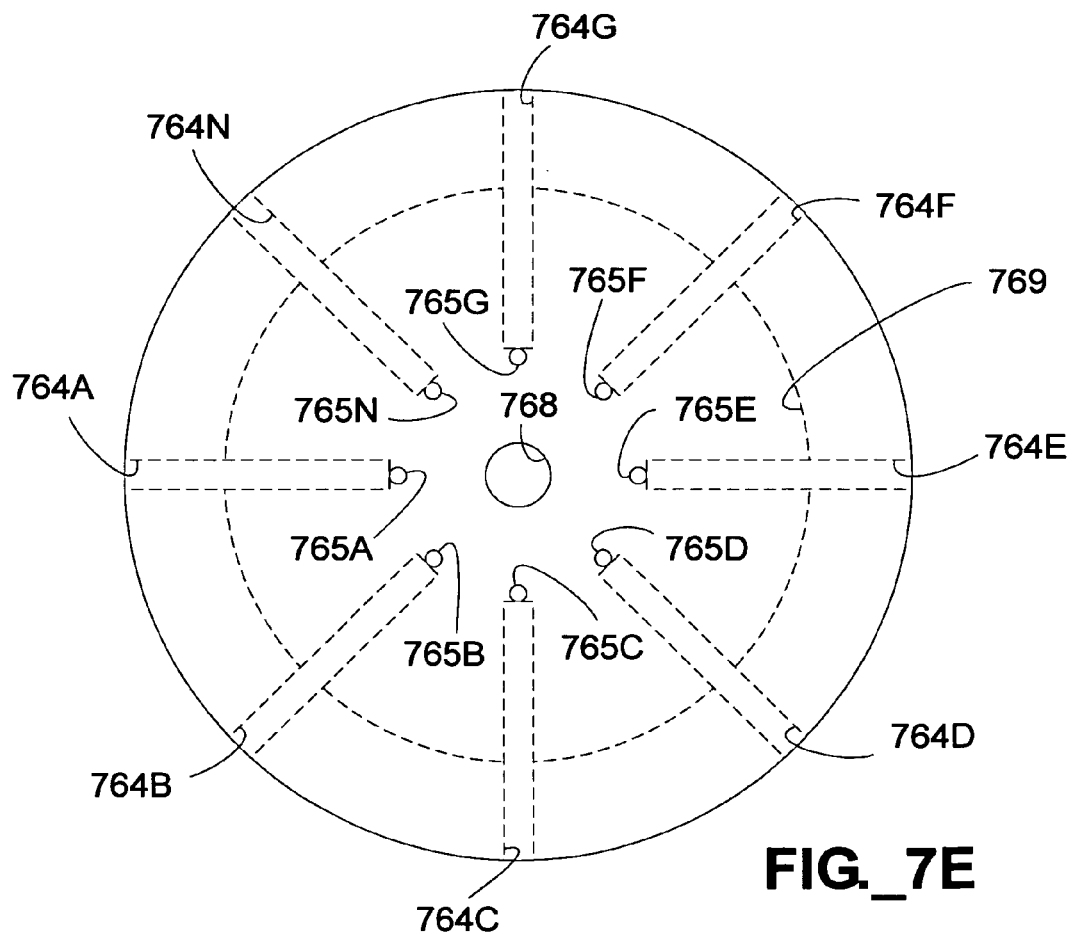
FIG._7E

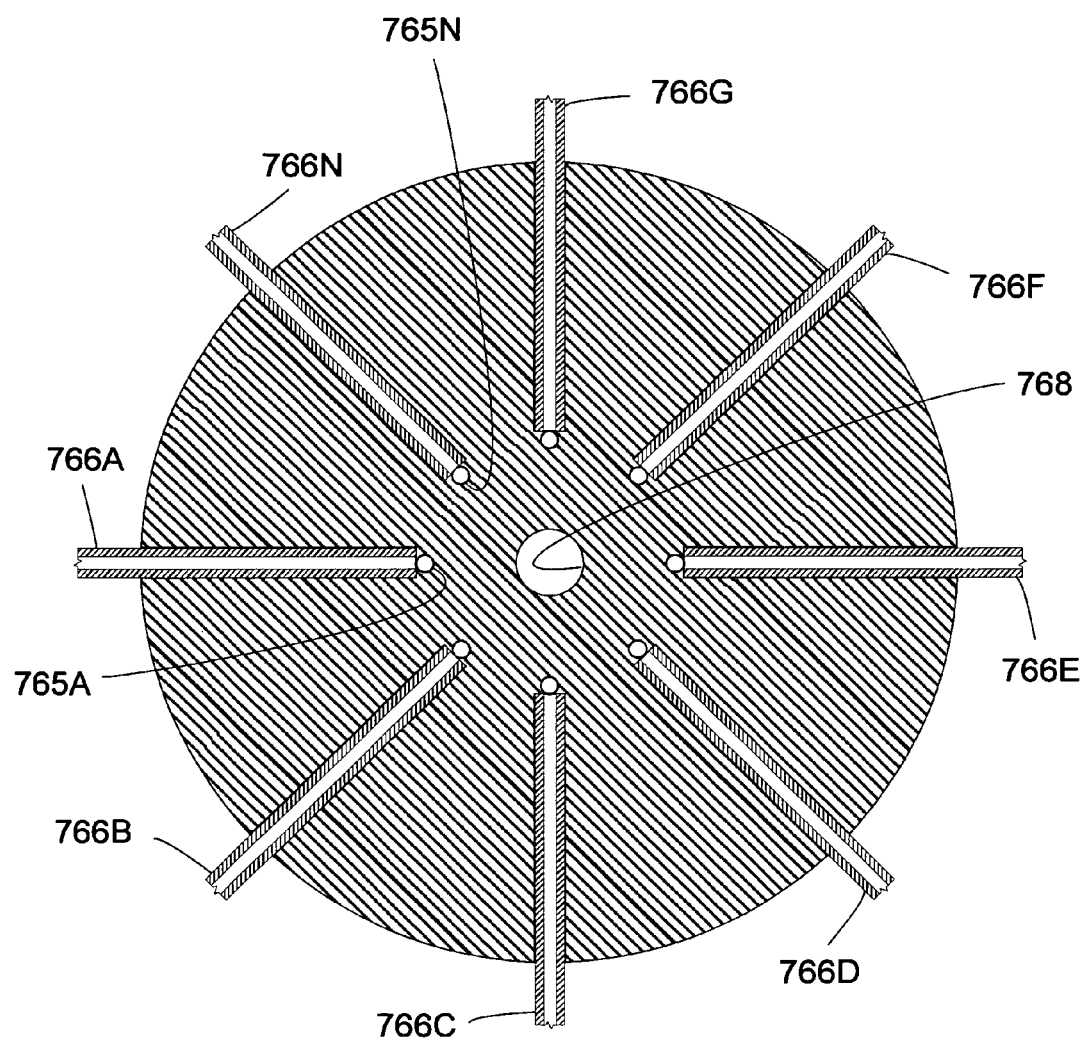
FIG._7F

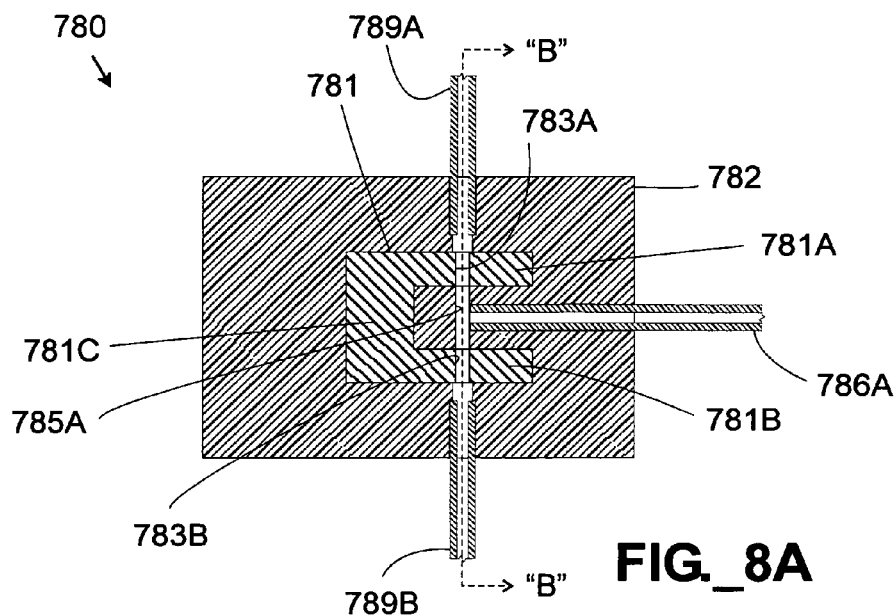
FIG._8A
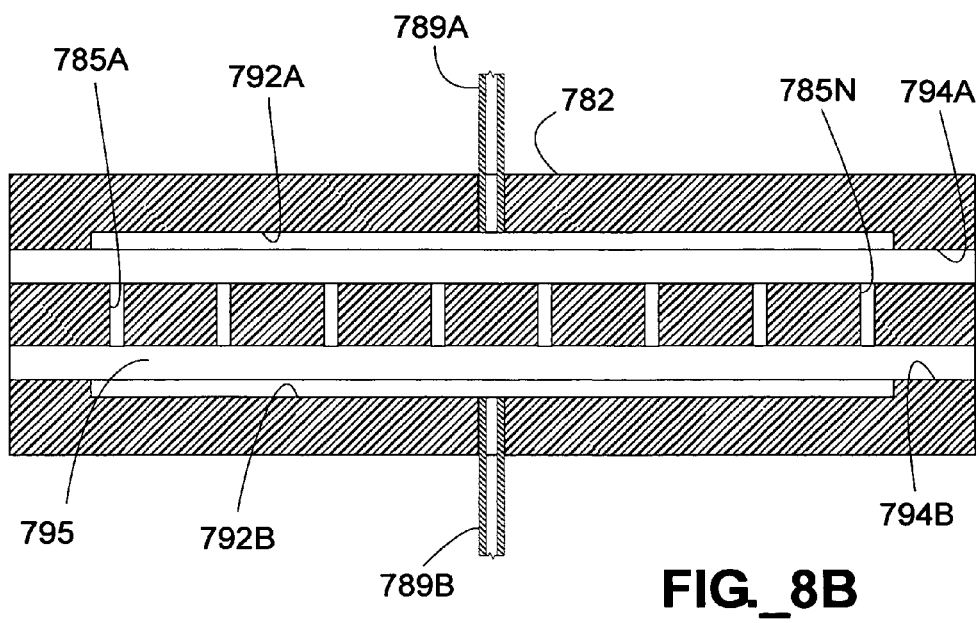
FIG._8B

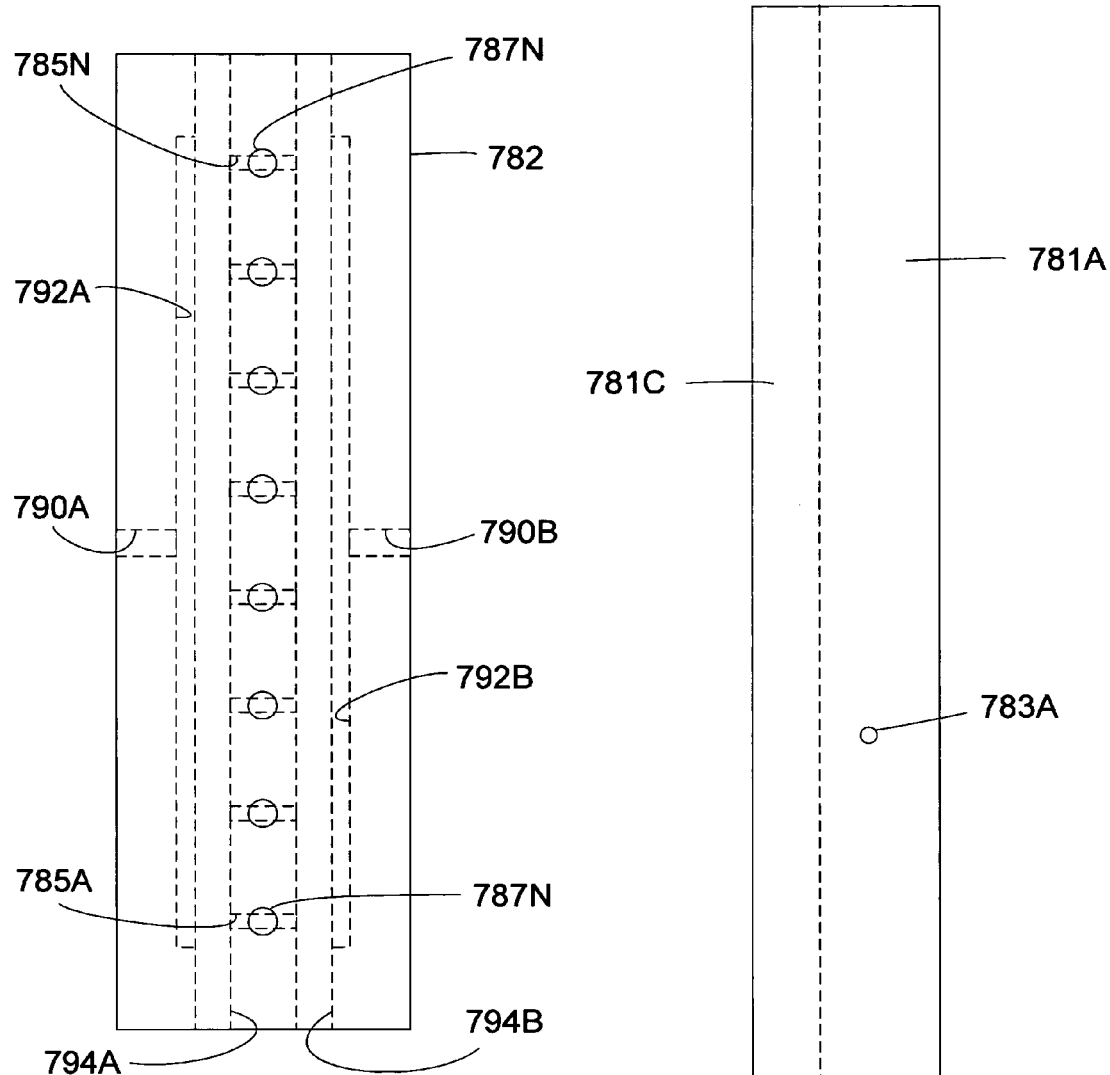

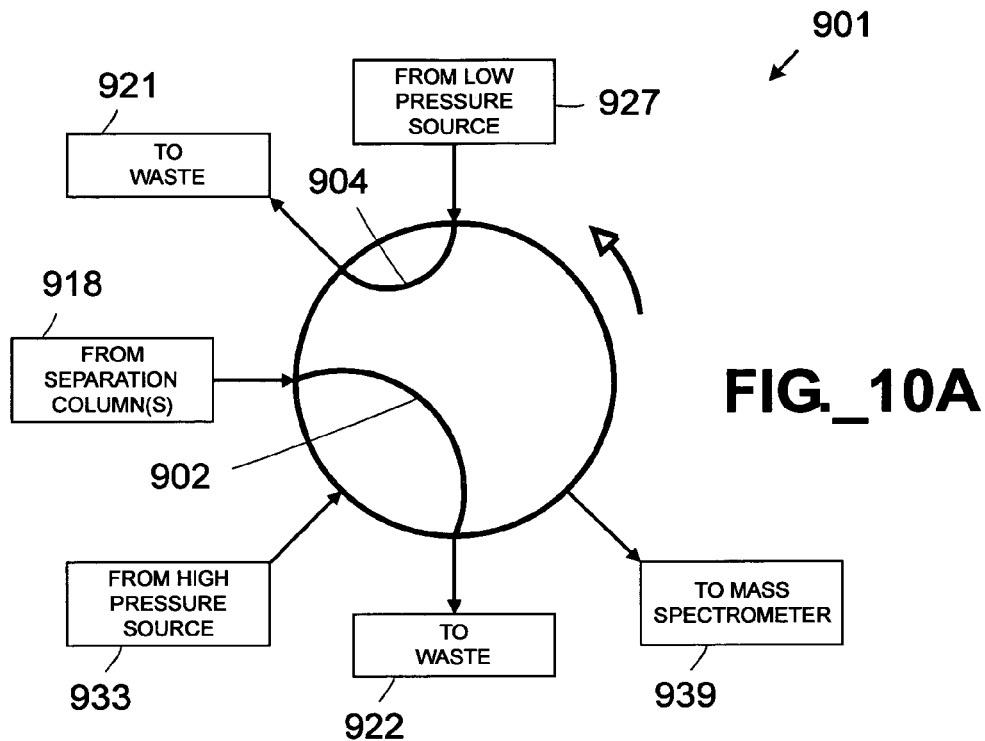
FIG._10A
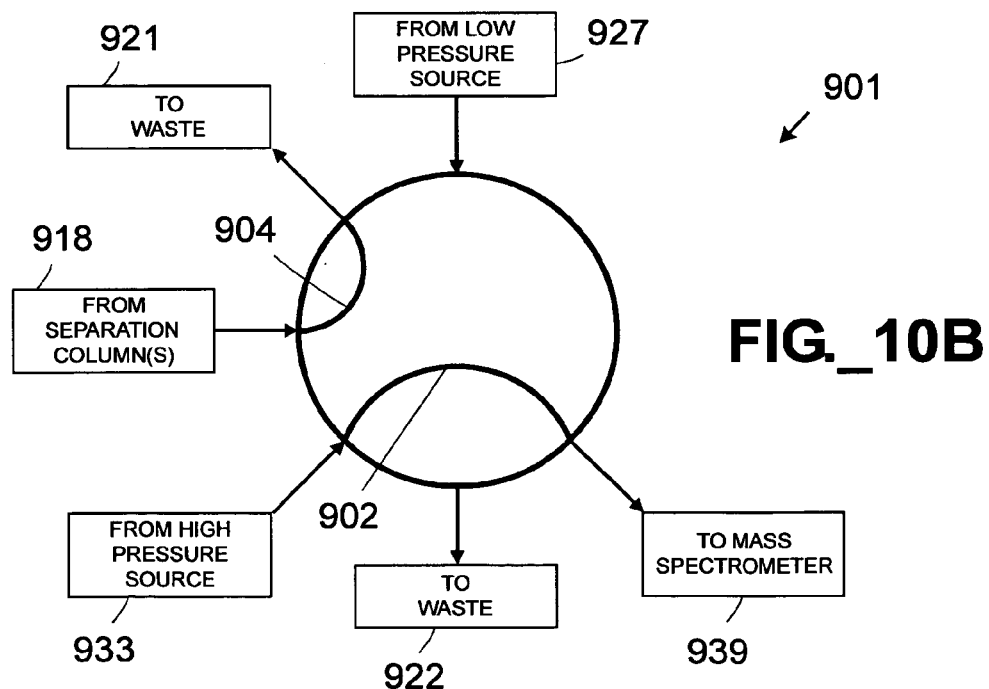
FIG._10B

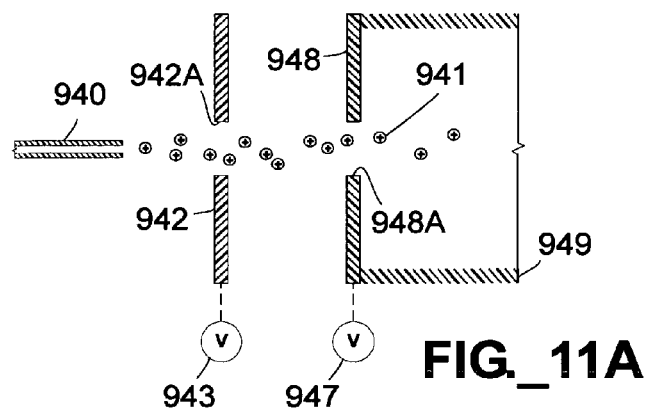
FIG._11A
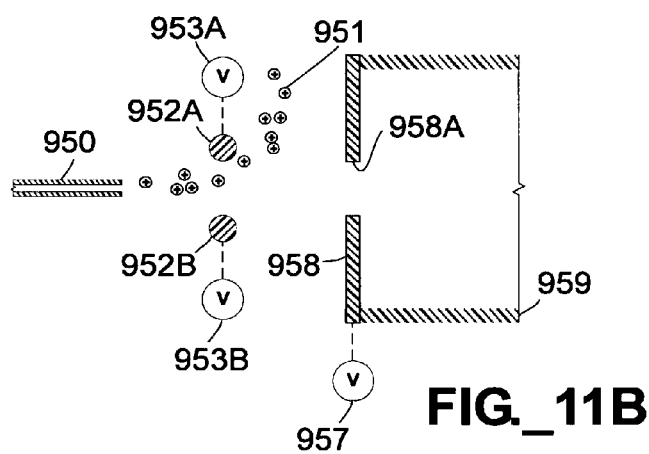
FIG._11B
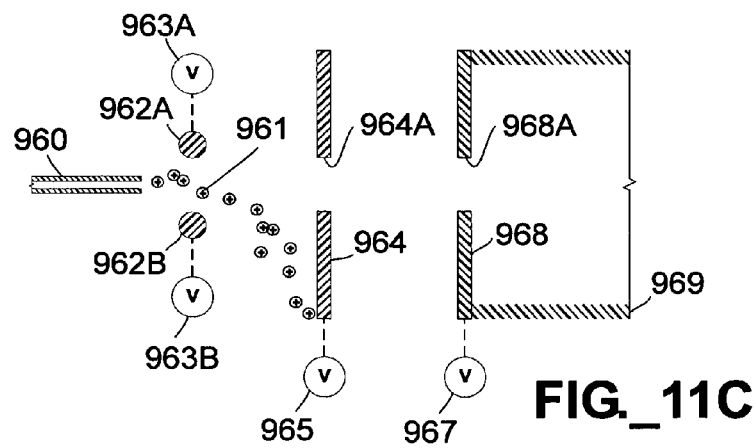
FIG._11C

HIGH THROUGHPUT MULTI-DIMENSIONAL SAMPLE ANALYSIS

FIELD OF THE INVENTION

The present invention relates to systems and methods employing multiple chromatographic separation columns coupled to a common mass spectrometer.

BACKGROUND OF THE INVENTION

Recent developments in the pharmaceutical industry and in combinatorial chemistry have exponentially increased the number of potentially useful compounds, each of which must be characterized in order to identify their active components and/or establish processes for their synthesis. To more quickly analyze these compounds, researchers have sought to automate analytical processes and to implement analytical processes in parallel.

One useful analytical process is chromatography, which encompasses a number of methods that are used for separating ions or molecules that are dissolved in or otherwise mixed into a solvent. Liquid chromatography ("LC") is a physical method of separation wherein a liquid "mobile phase" (typically consisting of one or more solvents) carries a sample containing multiple constituents or species through a separation medium or "stationary phase." Various types of mobile phases and stationary phases may be used. Stationary phase material typically includes a liquid-permeable medium such as packed granules (particulate material) disposed within a tube (or other channel boundary). The packed material contained by the tube or similar boundary is commonly referred to as a "separation column." High pressure is often used to obtain a close-packed column with a minimal void between each particle, since better resolution during use is typically obtained from more tightly packed columns. As an alternative to packed particulate material, a porous monolith or similar matrix may be used. So-called "high performance liquid chromatography" ("HPLC") refers to efficient separation methods that are typically performed at high operating pressures.

Typical interactions between stationary phases and solutes include adsorption, ion-exchange, partitioning, and size exclusion. Examples of types of stationary phases to support such interactions are solids, ionic groups on a resin, liquids on an inert solid support, and porous or semi-porous inert particles, respectively. Commonly employed base materials include silica, alumina, zirconium, or polymeric materials. A stationary phase material may act as a sieve to perform simple size exclusion chromatography, or the stationary phase may include functional groups (e.g., chemical groups) to perform other (e.g., adsorption or ion exchange separation) techniques.

Mobile phase is forced through the stationary phase using means such as, for example, one or more pumps, gravity, voltage-driven electrokinetic flow, or other established means for generating a pressure differential. After sample is injected into the mobile phase, such as with a conventional loop valve, components of the sample will migrate according to interactions with the stationary phase and the flow of such components are retarded to varying degrees. Individual sample components may reside for some time in the stationary phase (where their velocity is essentially zero) until conditions (e.g., a change in solvent concentration) permit a component to emerge from the column with the mobile phase. In other words, as the sample travels through voids or pores in the stationary phase, the sample may be separated into its constituent species due to the attraction of the species to the stationary phase. The time a particular constituent spends in the stationary phase relative to the fraction of time it spends in the mobile phase will determine its velocity through the column. Following separation in an LC column, the eluate stream contains series of regions having an elevated concentration of individual component species. Thus, HPLC acts to provide relatively pure and discrete samples of each of the components of a compound. Gradient separations using conventional HPLC systems are typically performed within intervals of roughly five to ten minutes, followed by a flush or rinse cycle before another sample is separated in the same separation column.

Following chromatographic separation in the column, the resulting eluate stream (consisting of mobile phase and sample) contains a series of regions having elevated concentrations of individual species, which can be detected by various flow-through techniques including spectrophotometric (e.g., UV-Vis), fluorimetric, refractive index, electrochemical, or radioactivity detection. Liquid chromatography with flow-through detection generally provides signal response that is proportional to analyte amount or concentration. As a result, LC is well suited for quantitative analysis, but it is difficult to identify or characterize individual components using only LC, particularly when novel or previously uncharacterized compounds are used.

Another important analytical technique that can complement LC analysis is mass spectrometry ("MS"). MS permits molecular mass to be measured by determining the mass-to-charge ratio ("m/z") of ions generated from target molecules. A mass spectrometer typically includes a source for generating ions from a sample and delivering them into the gas phase, an analyzer for separating and sorting the ions, and a detector for sensing the ions as they are sorted. MS is a fast analytical technique that typically provides an output spectrum displaying ion intensity as a function of m/z. The benefit of using MS is that it can provide unique information about the chemical composition of the analyte—information that is much more specific than that can be obtained using flow-through detectors used with most conventional LC systems. The ability to qualitatively identify molecules using MS complements the quantitative capabilities of LC, thus providing a second dimension to the chromatographic analysis.

Various mass spectrometric techniques are known, including time-of-flight ("TOF"), quadrupole, and ion trap. In a TOF analyzer, ions are separated by differences in their velocities as they move in a straight path toward a collector in order of increasing mass-to-charge ratio. In a TOF MS, ions of a like charge are simultaneously emitted from the source with the same initial kinetic energy. Those with a lower mass will have a higher velocity and reach the detector earlier than ions with a higher mass. In a quadrupole device, a quadrupolar electrical field (comprising radiofrequency and direct-current components) is used to separate ions. An ion trap (e.g., quadrupole-based) can trap and mass-analyze ions using a three-dimensional quadrupolar radio frequency electric field. In ion trap instruments, ions of increasing mass-to-charge ratio successively become unstable as the radio frequency voltage is scanned.

Various conventional ionization techniques may be used with mass spectrometry. One prevalent technique is electrospray ionization (ESI), which is a "soft" ionization technique. That is, ESI does not rely on extremely high temperatures or extremely high voltages to accomplish ionization, which is advantageous for the analysis of large, complex molecules that tend to decompose under harsh conditions. In ESI, highly charged droplets of analyte dispersed from a capillary in an electric field are evaporated, and the resulting ions are drawn into a MS inlet. Other known ionization techniques include: chemical ionization (which ionizes volatilized molecules by reaction with reagent gas ions); field ionization (which produces ions by subjecting a sample to a strong electric field gradient); spark-source desorption (which uses electrical discharges or sparks to desorb ions from samples); laser desorption (which uses a photon beam to desorb sample molecules); matrix-assisted laser desorption ionization or "MALDI" (which produces ions by laser desorbing sample molecules from a solid or liquid matrix containing a highly UV-absorbing substance); fast atom bombardment or "FAB" (which uses beams of neutral atoms to ionize compounds from the surface of a liquid matrix); and plasma desorption (which uses very high-energy ions to desorb and ionize molecules in solid-film samples).

By coupling the output of an HPLC system to a MS system, it becomes possible to both quantify and identify the components of a sample. There exist challenges, however, in providing efficient integrated HPLC/MS systems. Conventional MS systems are capable of much faster sample analysis than HPLC systems, and are much more expensive by a factor of roughly four to five times the cost of a single-column HPLC system. Integrated HPLC/MS systems including a single HPLC column coupled to a MS by way of an ESI interface are known, but they suffer from limited utility since the overall system throughput is limited by the HPLC column, which requires several minutes to separate a single sample. In other words, a HPLC/MS system having only a single HPLC column fails to utilize the rapid analytical capabilities of the MS portion efficiently.

HPLC/MS systems having multiple HPLC columns coupled to a single MS are also known and provide greater separation efficiency compared to single-column HPLC/MS systems; however, conventionally-coupled multi-column HPLC/MS systems still suffer from limited utility. Examples are provided in U.S. Pat. No. 6,410,915 to Bateman et al.; U.S. Pat. No. 6,191,418 to Hindsgaul et al.; U.S. Pat. No. 6,066,848 to Kassel et al.; and U.S. Pat. No. 5,872,010 to Karger et al., each showing some variation of a multiplexed HPLC/MS system where the outputs of multiple simultaneously-operated separation columns are periodically sampled by a single MS device. In these multiplexed HPLC/MS systems, the MS can sample an eluate stream from only one LC column at a given time. While one stream is being analyzed, the others must continue to flow, as these systems have no storage capacity. This inherently results in data loss. To mitigate this data loss, MS sampling must occur very quickly. The MS instrument thus receives very small plugs of sample, reducing the ability of the instrument to integrate data in order to eliminate noise and resulting in reduced signal clarity. Additionally, conventional multi-column HPLC/MS systems typically utilize mechanical "gating" for directing desorbed (i.e., ionized) eluate from multiple columns into a single MS inlet. Such systems are extremely complex and expensive to operate and maintain.

Accordingly, there exists a need for improved HPLC/MS systems that permit parallel analysis of multiple samples. Advantageous system characteristics would include scalability to permit a large number of samples to be analyzed simultaneously at a low cost per analysis with minimal loss of data and/or signal clarity. Ideally, an improved system would also be comparatively simple and inexpensive to build and operate.

BRIEF DESCRIPTION OF THE DRAWINGS

FIG. 1 is a top view of a multi-layer microfluidic device containing twenty-four separation columns suitable for performing pressure-driven liquid chromatography.

FIG. 2A is an exploded perspective view of a first portion, including the first through fourth layers, of the microfluidic device shown in FIG. 1.

FIG. 2B is an exploded perspective view of a second portion, including the fifth and sixth layers, of the microfluidic device shown in FIG. 1.

FIG. 2C is an exploded perspective view of a third portion, including the seventh and eighth layers, of the microfluidic device shown in FIG. 1.

FIG. 2D is an exploded perspective view of a fourth portion, including the ninth through twelfth layers, of the microfluidic device shown in FIG. 1.

FIG. 2E is a reduced size composite of FIGS. 2A–2D showing an exploded perspective view of the microfluidic device of FIG. 5.

FIG. 3A is an exploded perspective view of a multi-layer microfluidic device having two fluidic inlets and one fluidic outlet.

FIG. 3B is a top view of the device of FIG. 3A.

FIGS. 4A–4C are top views of the device of FIGS. 3A–3B in a first, second, and third state of operation, respectively.

FIG. 5 is a schematic of a first integrated, multi-channel liquid chromatography/mass spectrometer analysis system, the system having switchable banks of high-capacity capillary storage elements disposed between a group of chromatography columns and the inlet of a mass spectrometer.

FIG. 7A is a side cross-sectional view of a rotary multi-chamber storage device that may be used with the system of FIG. 6, the device including a stator element having multiple storage chambers for receiving eluate from multiple liquid chromatography columns and a rotor element permitting the contents of the storage chambers to be sequentially discharged into a mass spectrometer.

FIG. 7B is a side cross-sectional view of the rotor element of FIG. 7A.

FIG. 7C is a side cross-sectional view of the stator element of FIG. 7A.

FIG. 7D is a top view of the rotor element of FIGS. 7A and 7B.

FIG. 7E is a top view of the stator element of FIGS. 7A and 7C.

FIG. 7F is a top cross-sectional view of the stator element of FIGS. 7A, 7C, and 7E taken along section lines "A"–"A" as illustrated in FIG. 7C.

FIG. 8A is an end cross-sectional view of a sliding element multi-chamber storage device that may be used with the system of FIG. 6, the device including an outer stationary element having multiple storage chambers for receiving eluate from multiple liquid chromatography columns and a sliding element permitting the contents of the storage chambers to be sequentially discharged into a mass spectrometer.

FIG. 8B is a side cross-sectional view of the stationary element of FIG. 8A taken along section lines "B"–"B" as illustrated in FIG. 8A.

FIG. 8C is a top view of the stationary element of FIGS. 8A and 8B.

FIG. 8D is a top view of the sliding element of FIG. 8A.

FIGS. 10A and 10B are schematic views of loop-type rotary storage valves for use with an integrated liquid chromatography/mass spectrometer analysis system in a first and second state of operation, respectively.

FIG. 11A is a side cross-sectional view of a first electrically gated interface between an ionization element and a mass spectrometer inlet.

FIG. 11B is a side cross-sectional view of a second electrically gated interface between an ionization element and a mass spectrometer inlet.

FIG. 11C is a side cross-sectional view of a third electrically gated interface between an ionization element and a mass spectrometer inlet.

Figure 6:
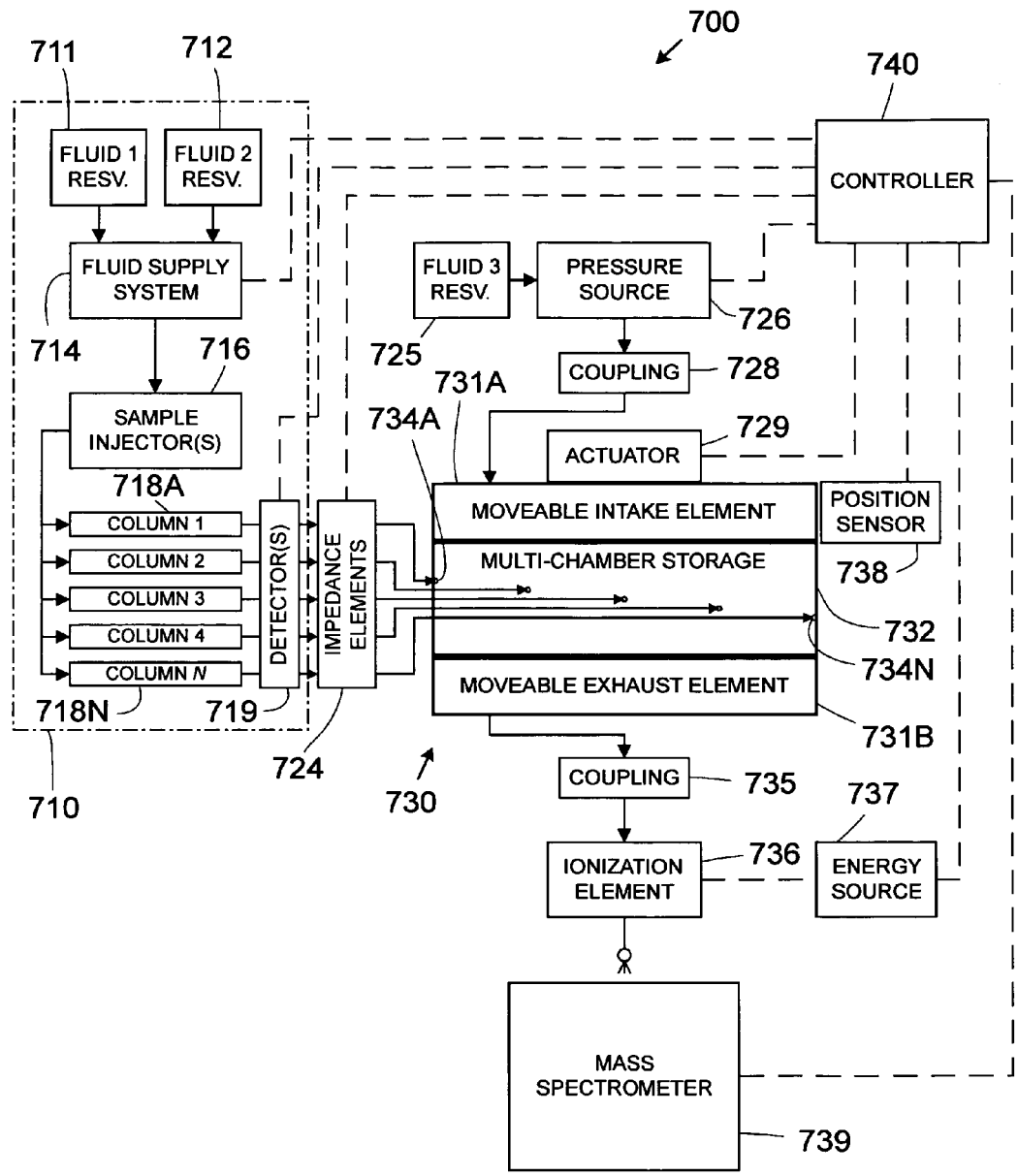
FIG. 6 is a schematic of a second integrated, multi-channel liquid chromatography/mass spectrometer analysis system, the system having multiple low-capacity storage chambers disposed between a group of chromatography columns and the inlet of a mass spectrometer.

None of the figures are drawn to scale unless indicated otherwise. The size of one figure relative to another is not intended to be limiting, since certain figures and/or features may be expanded to promote clarity in the description.

DETAILED DESCRIPTION OF PREFERRED EMBODIMENTS OF THE INVENTION

A. Definitions

The terms "column" or "separation column" as used herein are used interchangeably and refer to a region of a fluidic device that contains stationary phase material and is adapted to perform a separation process.

The term "fluidic distribution network" refers to an interconnected, branched group of channels and/or conduits capable of adapted to divide a fluid stream into multiple substreams.

The term "frit" refers to a liquid-permeable material adapted to retain stationary phase material within a separation column.

The term "liquid phase separation process region" as used herein refers to any region adapted to perform a liquid phase chemical or biochemical analytical process such as chromatographic, electrophoretic, electrochromatographic, immunoaffinity, gel filtration, and/or density gradient separation. A separation column is one type of a liquid phase separation process region.

The term "mass analyzer" as used herein refers to an analytical component that serves to separate ions electromagnetically based on their charge/mass ratio.

The term "microfluidic" as used herein refers to structures or devices through which one or more fluids are capable of being passed or directed and having at least one dimension less than about 500 microns.

The term "packed" as used herein refers to the state of being substantially filled with a packing material (such as a particulate material).

The term "parallel" as used herein refers to the ability to concomitantly or substantially concurrently process two or more separate fluid volumes, and does not necessarily refer to a specific channel or chamber structure or layout.

The term "plurality" as used herein refers to a quantity of two or more.

The term "slurry" as used herein refers to a mixture of particulate matter and a solvent, preferably a suspension of particles in a solvent.

The term "stencil" as used herein refers to a material layer or sheet that is preferably substantially planar through which one or more variously shaped and oriented portions have been cut or otherwise removed through the entire thickness of the layer, and that permits substantial fluid movement within the layer (e.g., in the form of channels or chambers, as opposed to simple through-holes for transmitting fluid through one layer to another layer). The outlines of the cut or otherwise removed portions form the lateral boundaries of microstructures that are formed when a stencil is sandwiched between other layers such as substrates and/or other stencils.

The terms "storage region," "storage element," and "storage chamber" as used herein are used substantially interchangeably and refer to any structure adapted to convey and store a fluid while maintaining the integrity of an output stream of a separation column, including, but not limited to tubes, conduits, channels, and chambers. A fluid fraction disposed within a storage region, storage element, or storage chamber should attain a zero velocity state at least momentarily.

Microfluidic Devices Generally

Traditionally, microfluidic devices have been fabricated from rigid materials such as silicon or glass substrates using surface micromachining techniques to define open channels and then affixing a cover to a channel—defining substrate to enclose the channels. There now exist a number of well-established techniques for fabricating microfluidic devices, including machining, micromachining (including, for example, photolithographic wet or dry etching), micromolding, LIGA, soft lithography, embossing, stamping, surface deposition, and/or combinations thereof to define apertures, channels or chambers in one or more surfaces of a material or that penetrate through a material.

A preferred method for constructing microfluidic devices utilizes stencil fabrication, which includes the lamination of at least three device layers including at least one stencil layer or sheet defining one or more microfluidic channels and/or other microstructures. As noted previously, a stencil layer is preferably substantially planar and has a channel or chamber cut through the entire thickness of the layer to permit substantial fluid movement within that layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. Various preferred embodiments utilize porous materials including filtration media. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties. For instance, particularly desirable polymers include polyolefins, more specifically polypropylenes, and vinyl-based polymers.

Various means may be used to seal or bond layers of a device together. For example, adhesives may be used. In one embodiment, one or more layers of a device may be fabricated from single- or double-sided adhesive tape, although other methods of adhering stencil layers may be used. Portions of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thickness of these carrier materials and adhesives may be varied.

Device layers may be directly bonded without using adhesives to provide high bond strength (which is especially desirable for high-pressure applications) and eliminate potential compatibility problems between such adhesives and solvents and/or samples. For example, in one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately five hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

Microfluidic Liquid Phase Separation (e.g., Chromatography) Devices

One advantage of performing a liquid phase separation process such as chromatography in a microfluidic format is that multiple separations can be performed in parallel with a single liquid phase separation system. Although the following examples are directed primarily to liquid chromatography system and devices, one skilled in the art will recognize that various different types of liquid phase separation processes, such as chromatographic, electrophoretic, electrochromatographic, immunoaffinity, gel filtration, and/or density gradient separations, may be utilized with the present invention utilizing the teachings provided herein.

If multiple chromatography columns are provided in a single separation device, then such a device preferably has at least one associated fluidic distribution network to permit operation with a minimum number of expensive (typically external) system components such as pumps and pulse dampers. One example of a multi-column microfluidic separation device suitable for performing pressure-driven liquid chromatography is provided in FIG. 1 and FIGS. 2A–2E. The device 400 includes twenty-four parallel separation channels 439A–439N containing stationary phase material. (Although FIG. 1 and FIGS. 2A–2E show the device 400 having eight separation columns 439A–439N, it will be readily apparent to one skilled in the art that any number of columns 439A–439N may be provided. For this reason, the designation "N" represents a variable and could represent any desired number of columns. This convention is used throughout this document.)

The device 400 may be constructed with twelve device layers 411–422, including multiple stencil layers 414–420 and two outer or cover layers 411, 422. Each of the twelve device layers 411–422 defines five alignment holes 423–427 (with hole 424 configured as a slot), which may be used in conjunction with external pins (not shown) to aid in aligning the layers during construction or in aligning the device 400 with an external interface (not shown) during a packing process or during operation of the device 400. Preferably, the device 400 is constructed with materials selected for their compatibility with chemicals typically utilized in performing high performance liquid chromatography, including, water, methanol, ethanol, isopropanol, acetonitrile, ethyl acetate, dimethyl sulfoxide, and mixtures thereof. Specifically, the device materials should be substantially non-absorptive of, and substantially non-degrading when placed into contact with, such chemicals. Suitable device materials include polyolefins such as polypropylene, polyethylene, and copolymers thereof, which have the further benefit of being substantially optically transmissive so as to aid in performing quality control routines (including checking for fabrication defects) and in ascertaining operational information about the device or its contents. For example, each device layer 411–422 may be fabricated from 7.5 mil (188 micron) thickness "Clear Tear Seal" polypropylene (American Profol, Cedar Rapids, Iowa).

Broadly, the device 400 includes various structures adapted to distribute particulate-based slurry material among multiple separation channels 439A–439N (to become separation columns upon addition of stationary phase material), to retain the stationary phase material within the device 400, to mix and distribute mobile phase solvents among the separation channels 439A–439N, to receive samples, to convey eluate streams from the device 400, and to convey a waste stream from the device 400.

The first through third layers 411–413 of the device 400 are identical and define multiple sample ports/vias 428A–428N that permit samples to be supplied to channels 454A–454N defined in the fourth layer 414. While three separate identical layers 411–413 are shown (to promote strength and increase the aggregate volume of the sample ports/vias 428A–428N to aid in sample loading), a single equivalent layer (not shown) having the same aggregate thickness could be substituted. The fourth through sixth layers 414–416 define a mobile phase distribution network 450 (including elements 450A–450N) adapted to split a supply of mobile phase solvent among twenty-four channel loading segments 454A–454N disposed just upstream of a like number of separation channels (columns) 439A–439N. Upstream of the mobile phase distribution network 450, the fourth through seventh layers 414–417 further define mobile phase channels 448–449 and structures for mixing mobile phase solvents, including a long mixing channel 442, wide slits 460A–460B, alternating channel segments 446A–446N (defined in the fourth and sixth layers 414–416) and vias 447A–447N (defined in the fifth layer 415).

Preferably, the separation channels 439A–439N are adapted to contain stationary phase material such as, for example, silica-based particulate material to which hydrophobic C-18 (or other carbon-based) functional groups have been added. One difficulty associated with prior microfluidic devices has been retaining small particulate matter within separation columns during operation. The present device 400 overcomes this difficulty by the inclusion of a downstream porous frit 496 and a sample loading porous frit 456. Each of the frits 456, 496 (and frits 436, 438) may be fabricated from strips of porous material, e.g., 1-mil thickness Celgard 2500 membrane (55% porosity, 0.209×0.054 micron pore size, Celgard Inc., Charlotte, N.C.) and inserted into the appropriate regions of the stacked device layers 411–422 before the layers 411–422 are laminated together. The average pore size of the frit material should be smaller than the average size of the stationary phase particles. Preferably, an adhesiveless bonding method such as one of the methods described previously herein is used to bond the device layers 411–422 (and frits 436, 438, 456, 496) together. Such methods are desirably used to promote high bond strength (e.g., to withstand operation at high internal pressures of preferably at least about 100 psi (690 kPa), more preferably at least about 500 psi (3450 kPa)) and to prevent undesirable interaction between any bonding agent and solvents and/or samples to be supplied to the device 400.

A convenient method for packing stationary phase material within the separation channels 439A–439N is to provide it to the device in the form of a slurry (i.e., particulate material mixed with a solvent such as acetonitrile). Slurry is supplied to the device 400 by way of a slurry inlet port 471 and channel structures defined in the seventh through ninth device layers 417–419. Specifically, the ninth layer 419 defines a slurry via 471A, a waste channel segment 472A, and a large forked channel 476A. The eighth device layer 418 defines two medium forked channels 476B and a slurry channel 472 in fluid communication with the large forked channel 476A defined in the ninth layer 419. The eighth layer 418 further defines eight smaller forked channels 476N each having three outlets, and twenty-four column outlet vias 480A–480N. The seventh layer 417 defines four small forked channels 476C in addition to the separation channels 439A–439N. In the aggregate, the large, medium, small, and smaller forked channels 476A–476N form a slurry distribution network that communicates slurry from a single inlet (e.g., slurry inlet port 471) to twenty-four separation channels 439A–439N (to become separation columns 439A–439N upon addition of stationary phase material). Upon addition of particulate-containing slurry to the separation channels 439A–439N, the particulate stationary phase material is retained within the separation channels by one downstream porous frit 496 and by one sample loading porous frit 456. After stationary phase material is packed into the columns 439A–439N, a sealant (preferably substantially inert such as UV-curable epoxy) is added to the slurry inlet port 471 to prevent the columns from unpacking during operation of the device 400. The addition of sealant should be controlled to prevent blockage of the waste channel segment 472A.

To prepare the device 400 for operation, one or more mobile phase solvents may be supplied to the device 400 through mobile phase inlet ports 464, 468 defined in the twelfth layer 422. These solvents may be optionally pre-mixed upstream of the device 400 using a conventional micromixer. Alternatively, these solvents are conveyed through several vias (464A–464F, 468A–468C) before mixing. One solvent is provided to the end of the long mixing channel 442, while the other solvent is provided to a short mixing segment 466 that overlaps the mixing channel 442 through wide slits 460A–460B defined in the fifth and sixth layers 415, 416, respectively. One solvent is layered atop the other across the entire width of the long mixing channel 442 to promote diffusive mixing. To ensure that the solvent mixing is complete, however, the combined solvents also flow through an additional mixer composed of alternating channel segments 446A–446N and vias 447A–447N. The net effect of these alternating segments 446A–446N and vias 447A–447N is to cause the combined solvent stream to contract and expand repeatedly, augmenting mixing between the two solvents. The mixed solvents are supplied through channel segments 448, 449 to the distribution network 450 including one large forked channel 450A each having two outlets, two medium forked channels 450B each having two outlets, four small forked channels 450C each having two outlets, and eight smaller forked channels 450N each having three outlets.

Each of the eight smaller forked channels 450A–450N is in fluid communication with three of twenty-four sample loading channels 454A–454N. Additionally, each sample loading channel 454A–454N is in fluid communication with a different sample loading port 428A–428N. Two porous frits 438, 456 are disposed at either end of the sample loading channels 454A–454N. While the first frit 438 technically does not retain any packing material within the device, it may be fabricated from the same material as the second frit 456, which does retain packing material within the columns 439A–439N by way of several vias 457A–457N. To prepare the device 400 for sample loading, solvent flow is temporarily interrupted, an external interface (not shown) previously covering the sample loading ports 428A–428N is opened, and samples are supplied through the sample ports 428A–428N into the sample loading channels 454A–454N. The first and second frits 438, 456 provide a substantial fluidic impedance that prevents fluid flow through the frits 438, 456 at low pressures. This ensures that the samples remain isolated within the sample loading channels 454A–454N during the sample loading procedure. Following sample loading, the sample loading ports 428A–428N are again sealed (e.g., with an external interface) and solvent flow is re-initiated to carry the samples onto the separation columns 439A–439N defined in the seventh layer 417.

While the bulk of the sample and solvent that is supplied to each column 439A–439N travels downstream through the columns 439A–439N, a small split portion of each travels upstream through the columns in the direction of the waste port 485. The split portions of sample and solvent from each column that travel upstream are consolidated into a single waste stream that flows through the slurry distribution network 476, through a portion of the slurry channel 472, then through the short waste segment 472A, vias 474C, 474B, a frit 436, a via 484A, a waste channel 485, vias 486A–486E, and through the waste port 486 to exit the device 400. The purpose of providing both an upstream and downstream path for each sample is to prevent undesirable cross-contamination from one separation run to the next, since this arrangement prevents a portion of a sample from residing in the sample loading channel during a first run and then commingling with another sample during a subsequent run.

Either isocratic separation (in which the mobile phase composition remains constant) or, more preferably, gradient separation (in which the mobile phase composition changes with time) may be performed. Following separation, the eluate may be analyzed by one or more detection techniques and/or collected for further analysis. Preferably, the eluate is analyzed using both flow-through optical-type detection (e.g., UV-Vis and/or fluorescence detection) and, subsequently, mass analysis such as mass spectrometry.

Other Multi-Column Chromatography Devices

Although multi-column microfluidic devices such as the device 400 are preferably used in an integrated multi-column HPLC/MS system, other formats, whether or not microfluidic, embodying multiple liquid phase separation process regions (e.g., columns) may be used. A multi-column HPLC apparatus may be any suitable device that includes multiple parallel separation columns. Multiple discrete tubular-type columns, multiple independent columns positioned within a single device, or any other suitable multi-column configuration may be used. It will be readily understood by one skilled in the art that any form or configuration of HPLC columns may be used, the appropriate column, fabrication method and stationary phase material being selected to match the performance characteristics required for the particular separation(s). Representative parallel HPLC column devices and fabrication methods are provided in commonly assigned U.S. patent application Ser. No. 10/638,258 entitled "Multi-Column Separation Devices and Methods" filed Aug. 7, 2003, the disclosure of which is hereby incorporated by reference as if fully set forth herein.

Minimizing Post-Separation Band Broadening

One general concern associated with interfacing multiple HPLC columns to a single MS is that eluate components separated from the chromatography process will "smear" or mix before the mass of such components can be analyzed by the MS. Several HPLC/MS interface systems and techniques disclosed herein include eluate storage capability disposed between a group of HPLC columns and the inlet of an associated MS. In certain embodiments, each eluate storage element includes sufficient volume to contain substantially all of the eluate flowing from a single column (i.e., to store an entire chromatogram). In such embodiments, the eluate storage elements are preferably microfluidic to minimize diffusion of separated bands of analyte and thereby preserve signal clarity. Commercially available capillary tubing of microfluidic internal dimensions may advantageously be used. If desired, the non-species-containing portions of the eluate (i.e., at the beginning and end of a chromatographic separation run) may be directed to waste through valves before the portion(s) of interest are stored in the eluate storage elements.

The volume of each storage element is preferably selected to accommodate the species segment of mobile phase output for a single chromatographic separation on its respective column 13A–13N. Thus, if the volume of the species segment of the mobile phase output of a separation is X microliters, the volume (V) of the storage line (V=$\pi$(0.5× ID)$^2$ x L, where ID is the inner diameter of the storage line and L is the length of the storage line) should be greater than or equal to X microliters. For example, a species segment having a volume of about 0.003 fl. oz. (about 100 microliters) requires an associated storage line having a length of approximately twenty-five feet (about seven and six tenth meters), assuming the internal diameter of the storage line is approximately five mils (about 130 microns). However, storing the species segments for long periods of time (e.g., many minutes) before MS analysis may be of concern as diffusion between the separated bands of analyte and the solvent may occur. Such diffusion could cause band broadening, thereby affecting the signal clarity of the sample as it is analyzed by the mass spectrometer. It has been found that maintaining microfluidic dimensions in the storage lines minimizes the size of the diffusion interface between bands and solvents, thereby mitigating band broadening. Moreover, it has been found that such diffusion produces a very small contribution to total band broadening compared to other features of the system (e.g., fluid inter-connections, valves, frits, etc.). As a result, there is considerable flexibility in the size of capillary tubing required to produce sufficient system performance.

Another concern is the degree of band broadening caused by the travel of the eluate stream through the entire length of the storage line. Band broadening in this context may be characterized by a band broadening factor (BF), which equals the ratio of peak width after passing through a storage line ("final peak width" or $W_x$) to peak width measured at the injector ("injector peak width" or $W_o$), (i.e., BF=$W_x$/$W_o$). Thus, if a one minute peak traveling through a seven meter storage line were to broaden to two minutes, the band broadening factor would be two (BF=2 min./1 min.=2). Another method for characterizing the band broadening is to determine the absolute or additive broadening (AB) factor, which is equal to the difference between the final peak width minus the injector peak width (i.e., $AB=W_x-W_o$). While both measures are useful, it has been found that the band broadening caused by travel through storage lines appears to be fixed or constant and not linear or geometric. Thus, in a storage line where a one-minute band is broadened to two minutes upon exiting the line, a two-minute band also is like to broaden by one minute. Accordingly, the additive broadening factor may be a more desirable measure of storage line performance.

An experiment was conducted using a test system, in which a reference analyte was provided from an injector directly into an ultraviolet (UV) detector. The same reference analyte was then introduced by an injector into a storage line and then to a UV detector located at the terminus of the storage line. The reference analyte was a 0.5 microliter plug of caffeine (2 milligrams/milliliter) introduced into a solvent flowing at 5 microliters/min. Table 1 shows the results of a comparison between storage lines fabricated with polyetheretherketone (PEEK) and stainless steel. Both experiments were performed using twenty-five foot (7.6 meter) storage lines with inner diameters of five mils (130 microns). Table 2 show the results of a similar experiment comparing the performance of PEEK storage lines having inner diameters of five and seven mils (130 and 180 microns, respectively) and lengths of twenty five feet (7.6 meters) and thirteen feet (four meters), respectively.

TABLE 1

Comparison of PEEK and Stainless Steel Storage Lines

| Material | W(x) (min) | W(o) (min) | BF | AB (min) |
|---|---|---|---|---|
| PEEK (5 mil) | 0.393 | 0.118 | 3.33 | 0.275 |
| SS (5 mil) | 0.604 | 0.118 | 5.12 | 0.486 |

TABLE 2

Comparison of Different Inner Diameters of PEEK Storage Lines

| ID (mil) | W(x) (min) | W(o) (min) | BF | AB (min) |
|---|---|---|---|---|
| 5 | 0.393 | 0.118 | 3.33 | 0.275 |
| 7 | 0.684 | 0.118 | 5.80 | 0.566 |

These experiments demonstrate that band broadening may be controlled by selecting the size/geometry and material properties of eluate storage lines. Thus, band broadening may be minimized by reducing the interior diameter of the storage lines and/or using a more hydrophobic material, such as PEEK. These parameters may be varied to tailor the system to the desired results. For example, wider or larger diameter storage lines may be used to accelerate processing where band resolution is not critical. Likewise, where band resolution is paramount, very narrow or smaller diameter storage lines may be used to minimize diffusion and broadening. Also, other materials, such as, but not limited to, polytetrafluoroethylene (PTFE), may be selected to further minimize or otherwise manipulate the behavior of the output stream in the storage lines. Suitable materials will be readily apparent to one skilled in the art.

Another strategy for reducing broadening or mixing between bands of separated eluate in storage lines includes providing a spacing medium between discrete bands. The spacing medium is preferably a fluid, more preferably a relatively inert gas such as nitrogen. A microfluidic device for introducing a spacing fluid into a flow of eluate is provided in FIGS. 3A–3B. The device 550 is constructed with five device layers 531–535. The first layer 531 serves as a cover. The second layer 532 defines a circular channel inlet 538 leading to a channel 539 in fluid communication with a short transverse segment 540. The third layer 533 defines a via 541 and an aperture 542 aligned below the segment 540 in the second layer 532. Although the aperture 542 could be formed in various shapes, it is preferably shaped as a narrow slit to minimize the contact distance along the narrow portion 544A of the primary channel 544 defined in the fourth layer 534, and thereby reduce volumetric uncertainty when separating an eluate stream into a fluidic plug. The fourth layer 534 defines a via 545 and a primary channel 544 composed of a narrow portion 544A and a wide portion 544B. The fifth layer 535 defines inlet ports 546, 548 for a first fluid and a second fluid, respectively, and a fluidic outlet port 559. The second fluid inlet port 548 is in fluid communication with the vias 538, 541, 545, which in turn provide a second fluid through the channel 539, short segment 540, and slit 542 to the channel 544 in the fourth layer 534. The five layers may be formed of various materials and may have various thicknesses sufficient to ensure that the internal channels are microfluidic scale. The assembled device 550 is shown in FIG. 3B. The operative features of the device 550 may be replicated so that one device portion 550 is provided downstream of each separation column of a multi-column HPLC system. A spacing device 550 having one or more functional regions may be provided in fluid communication with a multi-column HPLC device 400 (such as illustrated in and described previously in connection with FIGS. 1 and 2A–2E) by way of fluidic conduits, or the functional features of the spacing device 550 may be integrated directly into the separation device 400.

Operation of the spacing device according to the embodiment of FIGS. 3A–3B is shown in FIGS. 4A–4C. Referring to FIG. 4A, a first fluid (e.g., eluate from an HPLC column) is supplied through the first fluid inlet port 546 into the narrow channel segment 544A. As the first fluid 553 (shaded) fills the narrow portion 544A, it flows past the aperture 542 and into the wide portion 544B, as depicted in FIG. 4B. When a desired amount of the first fluid is present in the wide portion 544B of the primary channel 554 (composed of portions 544A, 544B), a second fluid having a pressure greater than that of the first fluid may be introduced to primary channel 554 by way of the second fluid inlet port 548 and channel 539. Preferably, the second fluid is a gas, such as (but not limited to) air, nitrogen, carbon dioxide, or argon. The second fluid 555 is communicated through the slit 542 into the narrow portion 544A where it separates the first fluid into a plug 553A. By either maintaining pressure within the first fluid or providing a check valve to prevent reverse flow of the first fluid, introduction of the second fluid to the primary channel 554 displaces the plug 553A in a direction toward the wide portion 544B and the outlet port 559. If the second fluid is a gas, one advantage of providing a narrow portion 544A and introducing the second fluid there is that a single pocket of gas filling the entire width of the portion 544A (and thereby separating the first fluid into a plug) is more readily formed, as opposed to a series of small bubbles not filling a channel that might result if a gas were to be introduced into a much wider channel. Providing a wide portion 544B permits the primary channel 554 to fill more slowly for a given total flow rate, which may be advantageous to reduce uncertainty in the volume of the resulting plug if there exists significant response delay in supplying the second fluid to the device 550. FIG. 4C shows the formation of a plug 553A of first fluid (e.g., eluate) following introduction of the second fluid 555 to the spacing device 550.

In contrast to the above-described embodiments having high-capacity storage elements, eluate storage elements in other embodiments include enough volume to contain only a small fraction of the eluate from one chromatographic separation run. In such instances, to permit a peak to be "reconstructed" from multiple pulses of analyte discharged from a storage element, each storage element may be selected to contain preferably less than about a third, more preferably less then about a fifth, even more preferably less than about an eighth, and still more preferably less than about a tenth of the eluate volume corresponding to the minimum peak width anticipated to be generated from a chromatographic separation run. [For example, if a selected chromatographic technique is capable of producing an analyte peak having a nominal width (e.g., full-width, half-max of one discrete analyte peak) of about ten seconds at a columnar flow rate of about 10 microliters/minute, then the fractional storage volume of a single storage element would preferably be less than about 0.56 microliters, more preferably less than about 0.33 microliters, even more preferably less than about 0.21 microliters, and still more preferably less than about 0.17 microliters.] Such low-volume systems should desirably be operated at a relatively rapid sampling rate, particularly when a large number of separation columns are provided in parallel. Since individual analyte peaks can be reconstructed from pulsed fractions, however, concerns about band broadening during the discharge of eluate to the MS are greatly reduced.

HPLC/MS System With Parallel High-Capacity Eluate Storaqe

In one embodiment, a multi-column HPLC/MS system includes parallel eluate storage capability. Commonly assigned U.S. Patent Application Publication No. 2004/0026617 filed Aug. 8, 2003 (that claims priority to Ser. No. 60/401,912 filed Aug. 8, 2002 and is hereby incorporated by reference as if set forth fully herein) discloses multi-column HPLC/MS systems having one high-capacity storage element (e.g., capillary storage lines) associated with each LC column. An improved HPLC/MS system 600 having parallel eluate storage capability to promote increased analytical throughput is illustrated in FIG. 5. One advantage of providing parallel eluate storage capability is that a first bank of storage elements (e.g., storage elements 628A) can be filled with eluate from a group of separation columns (e.g., columns 618A–618N) while storage elements (e.g., elements 628B) from a second bank are sequentially discharged into a mass spectrometer (e.g., mass spectrometer 639) for mass analysis. If desired, additional banks of capillary storage lines may be provided, to permit execution of additional functions (e.g., rinsing) on such storage lines while the first and second banks of capillary storage lines are being filled and discharged, respectively.

The system 600 includes an HPLC subsystem 610 and a MS interface subsystem 620 each in communication with a system controller 640. The HPLC subsystem 610 includes two fluid reservoirs 611, 612, such as may contain typical HPLC-grade solvents including liquids such as purified water, acetonitrile, methanol, isopropyl alcohol, or dimetylsulfoxide. A fluid supply system 614 (typically including multiple HPLC pumps) supplies solvents from the reservoirs 611, 612 to multiple separation columns 618A, 618N. Preferably, a mixer and splitting network (not shown) is disposed between the fluid supply system 614 and the columns 618A–618N. One or more sample injectors 616 (e.g., conventional loop-type sample injection valves or on-column sample injection means such as including the sample injection ports 428A–428N provided in the multi-column HPLC device 400 described previously) may be provided between the fluid supply system 614 and the HPLC columns 618A–618N. Following separation of sample in the columns 618A–618N, the resulting eluate flows through one or more suitable detectors (e.g., UV-Vis, fluorescent, or equivalent flow-through detector types) to the MS interface subsystem 620.

The MS interface subsystem 620 includes two parallel banks of storage elements 628A, 628B each preferably containing multiple capillary storage lines, with at least one storage line in each bank 628A, 628B associated with each column 618A–618N. In one embodiment, each individual storage line has sufficient volumetric capacity to store all the eluate of interest from an entire separation run performed in its corresponding separation column. Switching between the banks of parallel eluate storage elements 628A, 628B is provided by way of an upstream multi-channel output diverter 622 and a multi-channel input diverter 630. Each diverter 622, 630, which is preferably microfluidic to reduce band broadening, may include multiple discrete switching elements (e.g., multiple discrete valves, preferably valves with minimal dead volume) or may have the switching functions for multiple columns integrated into a single commonly-actuated multi-channel diverter device. Each individual storage element in the two storage banks 628A, 628B has an associated impedance element 624A, 624B and an individually actuatable purge initiation valve 625A–25N, 626A–626N, respectively. Each purge initiation valve 625A–625N, 626A–626N is in fluid communication with a pressure source 627A, 627B, preferably a source of pressurized relatively inert gas. The function of the purge initiation valves 625A–625N, 626A–626N is to periodically purge eluate from the storage lines into the mass spectrometer 639, with the impedance elements 624A–624N serving to prevent backflow of eluate or purge gas into the separation columns 618A–618N. The impedance elements 624A–624N may include actuated valves, passive check valves, or simply high impedance media such as microporous materials. Each storage element within the banks 628A, 628B may further include eluate retention means such as a microbore septum or actuated valve (not shown) immediately downstream of the storage element to retain eluate before it is purged through action of the purge initiation valves 625A–625N. The downstream multi-channel input diverter 630 is in selective fluid communication with each bank of upstream storage elements 628A, 628B and is in constant fluid communication with the ionization element(s) 636 disposed downstream. While any of the various ionization types mentioned herein may be used, a preferred ionization means is electrospray ionization. An energy source (not shown) such as including a voltage source (to provide electric ionization potential) with a source of heated gas (to promote evaporation of the solvent portion of the eluate) is preferably associated with the ionization element(s) 636. A multi-port switching valve 638 such as a rotary valve with a (e.g., low speed) rotating inlet aperture may be disposed downstream of the ionization element(s) 636 if multiple ionization elements (such as multiple electrospray needles, one associated with each column 618A–618N) are provided and immediately upstream of the inlet to a mass spectrometer 639. Alternatively, a collection manifold (not shown) may be disposed between the input diverter 630 and a single ionization element 636 to eliminate with the need for a switching valve 638.

In operation of the system 600, the HPLC columns 618–618N and mass spectrometer 639 may operate on a substantially continuous basis. While the contents of storage elements from a first bank (e.g., storage bank 628A) are being sequentially purged into the MS, the storage elements of a second bank may be receiving eluate from the HPLC columns 618A–618N, and vice-versa. In one embodiment, an additional diverter (not shown) may be provided immediately downstream of the columns 618A–618N to divert undesirable portions of the eluate streams to waste. The system controller 640 is preferably microprocessor-based and includes both hardware and software components to receive control inputs and permit execution of user-defined instruction sets. The controller 640 may include multiple discrete control elements including industrial controllers, personal computers, or similar control components, which may advantageously be networked or otherwise connected to permit communication between control components.

Electrical Gating of Ionized Analyte Molecules

In another embodiment, a multi-column HPLC/MS system may utilize electrical gating between an ionization source and the inlet of a mass spectrometer rather than conventional mechanical gating mechanisms such as rotary valves. Advantages of electrical gating include reliability due to the lack of moving parts, rapid switching facilitated by the use of high-frequency electrical switches, and easy modification of switching rates and switching routines through software control of the electrical switching apparatus. FIGS. 11A–11C show three different electrically gated interfaces each between an ionization source and an inlet of a mass spectrometer. In a multi-column system having at least one gate associated with each separation column, a manifold (not shown) for receiving ionized analyte from each column may be disposed between the gates and the inlet of a mass spectrometer, preferably with a flow of pressurized gas to sweep ionized molecules down the length of the manifold toward the MS.

Conventional MS inlets include ion focusing elements that are typically charged to direct the path of ions flowing therethrough. Various ion focusing elements are known and usually include an orifice in an electrically charged plate or other surface. Electrical ion gates according to embodiments provided herein are intended to be used upstream of and in conjunction with ion focusing elements. Various electrical ion gating configurations may be used. In one embodiment, an electrical ion gate includes an orifice in a charged plate or other surface. In another embodiment, an electrical ion gate includes one or more charged rods or poles slightly offset from the ejection axis of an ionization source outlet. In another embodiment, multiple electrical ion gates may be placed in series to provide enhanced control.

FIG. 11A shows a first electrically gated interface. An ionization source outlet 940 ejects charged ions 941 in the direction of a mass spectrometer 949, itself having a focusing element 948 defining an inlet orifice 948A and connected to a voltage source 947. A plate-type electrical gate 942 defining a central orifice 948A and connected to a voltage source 943 is disposed between the ionization source outlet 940 and the mass spectrometer inlet orifice 948A. In the present example, the output of the voltage source 943 connected to the electrical gate 942 is adjusted to a first state to permit ions 941 to flow straight through the gating orifice 942A and into the mass spectrometer inlet/focusing orifice 948A. Alternatively, the output of the voltage source 943 could be adjusted to disallow ions 941 from ever reaching the mass spectrometer inlet orifice 948A. For example, if the ions 941 are positively charged, then a high negative voltage could be applied to the ion gate 942 to draw ions "outward" from an axial path to either contact the gate 942 or scatter outward just downstream of the gate 942 to prevent the ions 941 from entering the orifice 948A of the focusing element 948.

An example of an embodiment having an electrical ion gate configured as one or more rods or poles is provided in FIG. 11B. An ionization source outlet 950 ejects charged ions 951 in the direction of a mass spectrometer 959 having a focusing element 958 defining an inlet orifice 958A and connected to a voltage source 957. An ion gate having two charged rods 952A, 952B is slightly offset from a straight linear path between the ionization source outlet 950 and the mass spectrometer inlet orifice 958A. Each rod 952A, 952B is connected to an independent voltage source 953A, 953B to permit the voltage to each gating rod 952A, 952B to be separately controlled. In the present example, the voltages provided to the first rod 952A and the second rod are adjusted to deflect the ions 951 upward and away from the mass spectrometer inlet orifice 958A. If the ions 951 are positively charged, then one method of accomplishing this deflection is to provide a negative voltage to the first rod 952A and a positive voltage to the second rod 952B. The ions 951 will thus be deflected toward the negatively charged first rod and away from the positively charged second rod 952B. Alternatively, the voltages provided to the gating rods may be adjusted to permit ions 951 to flow straight in the direction of the mass spectrometer inlet orifice.

An example of an embodiment having multiple focusing gates disposed in series is provided in FIG. 11C. An ionization source 960 ejects charged ions 961 in the direction of a mass spectrometer 969 having a focusing element defining an inlet orifice 968A and connected to a voltage source 957. A first rod-type ion gate having two charged rods 962A, 962B each connected to a different voltage source 963A, 963B is disposed downstream of the ionization source 960, with a second plate-type ion gate 964 defining a central orifice 964A disposed downstream of the rods 962A, 962B. One advantage of providing multiple ion gates in series is greater control of the gating function. In the example shown in FIG. 11C, positively charged ions 961 discharged from the ionization source outlet 960 are deflected (downward) by the providing a positive voltage to the first rod 962A and providing a negative voltage to the second rod 962B. The voltage supplied to the plate-type ion gate may also be adjusted to reinforce the ion deflection. If desired, ion collection electrodes (not shown) having an opposite charge polarity from the ions 961 may be disposed at the terminus of a deflected ion path to aid in the deflection process and to attract and gather ions not intended to be analyzed by the mass spectrometer 969.

HPLC/MS Systems With Low-Capacity Eluate Storage

As discussed previously, eluate storage elements in certain embodiments preferably include enough volume to contain only a small fraction of the eluate from one chromatographic separation run. The contents of such low-capacity eluate storage elements are preferably discharged frequently to a mass spectrometer, preferably by a sequential pulsed fraction injection method. One example of a system having multiple low-capacity eluate storage element suitable for performing pulsed fraction injection HPLC/MS analyses is illustrated in FIG. 6. The system 700 includes an HPLC subsystem 710 and a MS interface subsystem (not separately numbered but including the balance of elements provided in FIG. 6) each in communication with a system controller 740. The HPLC subsystem 710 includes two fluid reservoirs 711, 712, typically containing HPLC-grade solvents. A fluid supply system 714 (typically including multiple HPLC pumps) supplies solvents from the reservoirs 711, 712 to multiple separation columns 718A, 718N. One or more sample injectors 716 may be provided between the fluid supply system 714 and the HPLC columns 718A–718N. Following separation of sample in the columns 718A–718N, the resulting eluate flows through one or more suitable detectors 719 (e.g., UV-Vis, fluorescent, or similar flow-through detector types) to downstream MS interface components.

One or more impedance elements 724 are preferably provided downstream of the detector(s) 719. The impedance elements 724 serve to prevent backflow of eluate or purge gas into the separation columns 718A–718N. The impedance elements 724 may include actuated valves, passive check valves, or simply high impedance media such as microporous materials. A multi-chamber storage element 730 receives eluate from the impedance elements 724 through inlet ports 734A–734N. Preferably, a separate low-capacity chamber and associated inlet port 734A–734N is provided for each column 718A–718N of the group of columns 718A–718N. Fluid communication between the impedance elements and the multi-chamber storage element 730 is preferably provided by capillary tubes or equivalent microfluidic conduits. The multi-chamber storage element 730 preferably includes a stationary portion and a moveable portion and is designed to facilitate sequential purging of the contents of each storage chamber into the inlet of a mass spectrometer 739. Preferably, each storage chamber is located within the stationary portion to simplify the routing of fluidic conduits to the chambers. In one embodiment, the multi-chamber storage element 730 includes a moveable intake portion 731A, a moveable exhaust portion 731B, and a stationary portion 732. At least one actuator 729 is preferably provided to move the moveable portion(s) 731A, 731B, and a sensor 738 is preferably provided to sense characteristics of the storage element (or portions thereof) such as position, velocity, and/or acceleration. The moveable portions 731A, 731B are preferably linked together to move in tandem; however, such portions 731A, 731B can be independently actuated if desired. A pressure source 726, preferably including a reservoir 725 containing pressurized inert gas, is in fluid communication with the multi-chamber storage element 730. If the pressure source 726 is in fluid communication with moveable portion(s) of the multi-chamber storage element 730, then coupling elements 728, 735 are preferably provided. For example, if the multi-chamber storage element 730 is capable of rotary motion, then the coupling elements 728, 735 preferably permit rotary motion of any associated fluidic conduits to prevent kinking or breakage of such conduits. The multi-chamber storage element 730 serves to sequentially purge the contents of each individual storage element contained within the multi-chamber storage element 730, such as through application of pressurized gas from the pressure source 726. Downstream of the multi-chamber storage element 730, one or more ionization element(s) 736 are provided to ionize analyte molecules to prepare for their introduction into a mass spectrometer 739. While any of the various ionization types mentioned herein may be used, a preferred ionization means is electrospray ionization. An energy source 737 such as including a voltage source (to provide electric ionization potential) with a source of heated gas (to promote evaporation of the solvent portion of the eluate) is preferably associated with the ionization element(s) 736.

In operation of the system 700, eluate from each column 718A–718N is supplied in parallel to different storage chambers of the multi-chamber storage element 730. Each storage element may be designed to contain preferably less than about a third, more preferably less then about a fifth, even more preferably less than about an eighth, and still more preferably less than about a tenth of the eluate volume corresponding to the minimum peak width anticipated to be generated from a chromatographic separation run. Each storage element is sequentially discharged ahead of a pulse of pressurized gas supplied by the pressure source 726. The discharge frequency should be selected to roughly correspond to the filling frequency of each storage chamber. In one example, each storage chamber is discharged preferably at least once about two seconds, more preferably at least once about every second, yet more preferably at least once twice per second, and still more preferably at least once about five times per second. Eluate from each storage chamber is provided to the ionization element(s) 736 preferably by way of a coupling 735. The ionization element may optionally receive an additional supply of make-up fluid (not shown), such as may be useful to provide sustained electrospray ionization without undue sputter between receipt of pulses of eluate from the multi-chamber storage element 730. Alternatively, a variable volume bladder or equivalent damper (not shown) may be provided to reduce undesirable pressure pulses to the ionization element 736. Notably, the multi-chamber intake element may contain a surplus storage chamber for containing a "marker" or "reference" fluid (such as may be provided by a discrete fluid reservoir (not shown)) to be provided in sequence to the mass spectrometer 739 with the other eluate fractions to aid in identifying, at least once per cycle, the starting point of a new purge cycle of the multi-chamber storage element 730.

One example of a rotary-style multi-chamber storage element or device that may be used with the system 700 of FIG. 6 is illustrated in FIGS. 7A–7F. The storage device 760 includes a moveable rotor portion 761 and a stationary stator portion 762. The stator 762 defines multiple eluate storage chambers 765A–765N, each having a corresponding radial channel 764A–764N in fluid communication with a storage chamber 765A–765N. Preferably, to minimize inter-component dead volumes in conveying eluate within a HPLC/MS system, each radial channel 764A–764N is adapted to receive a different capillary tube such as the tubes 766A–766N to abut the storage chambers 765A–765N. The stator 762 defines a central bore 768 for receiving the shaft portion 761B of the rotor 761, and defines a lower recess 769 for receiving the exhaust portion 761C of the rotor 761. The stator further includes an upper sealing surface 772 and a lower sealing surface 774 for mating with the sealing surfaces 771, 773, respectively, of the stator.

The rotor 761 is preferably formed in multiple sections including an upper intake portion 761A, a connecting shaft portion 761B, and a lower exhaust portion 761C so that at least two of the portions 761A–761C can be assembled around the stator 762. The intake portion 761A defines a lower sealing surface 771 and the exhaust portion 761C defines an upper sealing surface 773. The intake portion 761A and the exhaust portion 761B define a purge fluid (e.g., gas) intake port 763A and a purge fluid/eluate exhaust port 763B, respectively. Preferably, the intake port 763A and exhaust port 763B are aligned with one another and disposed the same radial distance from the center axis of the device 760 as the eluate storage chambers 765A–765N.

Preferably, the rotor 761 and stator 762 are manufactured with extremely high dimensional tolerances to provide sealing engagement between the appropriate sealing surfaces 771–774 at elevated operating pressures. Any suitable manufacturing techniques and materials may be used to fabricate the rotor 761 and stator 762, including but not limited to conventional machining, micromachining, molding, sintering, etching, and combinations thereof. To facilitate high strength, durability, and wear resistance, preferred fabrication materials for the rotor 761 and stator 762 include ceramics, crystalline materials including ruby and sapphire, metals including advanced liquid metals, durable polymers, and/or composites. Suitably durable and inert low-friction coatings may be used along mating surfaces if desired. Mating surfaces 771–774 are preferably lapped and polished to facilitate high-pressure sealing. One or more (preferably peripherally outward from the storage chambers 765A–765N) raised features (not shown) (e.g., annular features sharing a common central axis with the device 760) and corresponding radial recesses may be provided in the sealing surfaces 771–774 of the rotor/stator combination to maximize sealing contact between the rotor 761 and stator 762.

Actuation of the rotor 761 or portions thereof may be performed with conventional actuating components such as one or more of: a motor, a stepper motor, a solenoid, a piston, a cam/follower, and a four-bar mechanism. The rotor 761 may move at a constant angular velocity, or in an accelerated start-stop fashion to minimize the delay time between the purge of each different chamber. In operation of the device 760, eluate is supplied continuously to each storage chamber 765A–765N by way of capillary conduits 766A–766N. Motion of the rotor 761 sequentially aligns the intake port 763A and exhaust port 763B with each storage chamber 765A–765N to cause a purge fluid (e.g., inert gas) to purge the eluate contents of each storage chamber downstream toward a mass spectrometer.

In another embodiment designed to promote higher storage density within a rotary multi-chamber storage device, storage chambers may be defined in concentric circles in a stator so long as corresponding intake and exhaust ports are defined in the corresponding rotor. In such an embodiment, the radial position of each storage chamber is preferably staggered to prevent simultaneous purging of multiple eluate storage chambers.

While rotary embodiments are preferred, an example of a sliding-type multi-chamber storage element or device that may be used with the system 700 of FIG. 6 is illustrated in FIGS. 8A–8D. The storage device 780 includes an outer stationary element 782 defining multiple storage chambers 785A–785N for receiving eluate from multiple liquid chromatography columns, and includes a sliding element 781 permitting the contents of the storage chambers 785A–785N to be sequentially purged or discharged into a downstream mass spectrometer. Each storage chamber 785A–785N has a corresponding channel 787A–787N in fluid communication with the chamber 785A–785N and preferably adapted to receive eluate from a different capillary conduit 786A–786N abutting the storage chamber 785A–785N. A "squared-C-shaped" aperture 795 corresponding in size and shape to the sliding element 781 is defined through the stationary element 782 to receive the sliding element 781. The aperture 795 includes upper and lower sealing surfaces 794A, 794B intended to slidingly engage the upper and lower surfaces, respectively, of the sliding element 781. The stationary element 782 further defines a purge fluid inlet port 790A, a purge fluid inlet distribution channel 792B, an eluate/purge fluid collection outlet channel 792B, and an eluate/purge fluid outlet port 790B.

The sliding element 781 may be formed as one integral part or from multiple parts, and may include an upper intake portion 781A, a lower exhaust portion 781B, and a connecting portion 781C. One advantage of connecting the intake and exhaust portions 781A, 781B via the connecting portion 781 is that the intake and exhaust portions 781A, 781B can be actuated in unison with a common actuator (not shown). In another embodiment, separate (i.e., unconnected) sliding intake and exhaust elements each having a dedicated actuator may be substituted. The sliding element 781 defines purge fluid inlet port 783A and an eluate/purge fluid outlet port 783B preferably adapted to receive a purge fluid inlet capillary 789A and an eluate/purge fluid outlet capillary 789B, respectively. The same general fabrication notes regarding the previous rotary multi-chamber storage device 760 apply equally to the present sliding multi-chamber storage device 780.

Actuation of the sliding element 781 may be performed with conventional actuating components such as one or more of: a worm drive, a rotary device and corresponding toothed rack, a solenoid, and a piston. Preferably, the actuating means is reversible to facilitate return of the sliding element to a starting position when one purge cycle is complete.

In operation of the multi-chamber storage device 780, each storage chamber 785A–785N receives eluate from a different separation column of a multi-column HPLC system. The sliding element 781 is translated within the recess 795 of the stationary element 782 to sequentially align the purge fluid inlet port 783A and an eluate/purge fluid outlet port 783B with each storage chamber 785A–785N. Pressurized purge fluid (e.g., pressurized inert gas) supplied into the purge fluid inlet distribution channel 792B by way of the purge fluid inlet port 783A sequentially forces the eluate contents of each storage chamber 785A–785N through the eluate/purge fluid collection outlet channel 792B and eluate/purge fluid outlet port 783B to exit the multi-chamber device 780 toward the inlet of a downstream mass spectrometer for subsequent mass analysis. After each storage chamber 785A–785N is sequentially purged, the sliding element 781 is returned to a starting position to re-start the sequential purge cycle. To prevent unwanted discharge of the storage chambers during the return of the sliding element to a starting position, supply of purge fluid may be temporarily interrupted, such as by closing an external valve (not shown).

Figure 9:
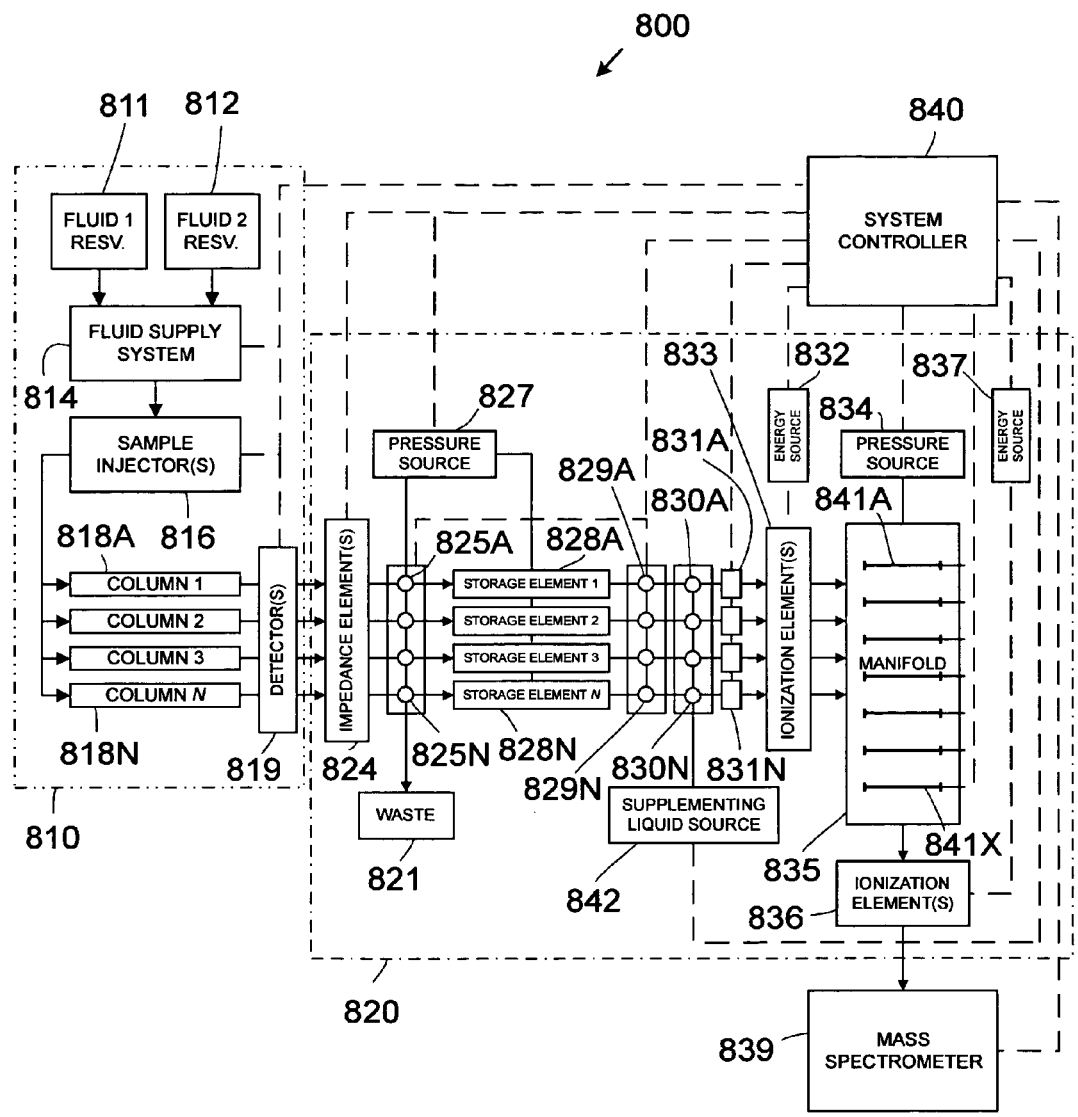
FIG. 9 is a schematic of a third integrated, multi-channel liquid chromatography/mass spectrometer analysis system, the system having multiple storage chambers and a collection manifold disposed between a group of chromatography columns and the inlet of a mass spectrometer.

Another multi-column HPLC/MS system with low-capacity eluate storage capability is illustrated in FIG. 9. The system 800 includes an HPLC subsystem 810 and a MS interface subsystem 820 each in communication with a system controller 840. Multiple controllers 840, either providing redundant or complementary functionality, may be provided if desired. The HPLC subsystem 810 includes two fluid reservoirs 811, 812 and a fluid supply system 814 (typically including multiple HPLC pumps) that supplies solvents from the reservoirs 811, 812 to multiple separation columns 818A, 818N (or other liquid phase separation process regions). One or more sample injectors 816 may be provided between the fluid supply system 814 and the HPLC columns 818A–818N. Following separation of sample in the columns 818A–818N, the resulting eluate flows through one or more suitable detectors 819 to downstream MS interface components.

One or more impedance elements 824 are preferably provided downstream of the detector(s) 819. The impedance elements 824, which may include actuated valves, passive check valves, or simply high impedance media such as microporous materials, serve to prevent backflow of eluate or purge gas into the separation columns 818A–818N when each storage element 828A–828N is purged, e.g., by intermittent supply of pressurized gas from a first (upstream) pressure source 827. Multiple storage chambers or regions 828A–828N are provided, preferably with one storage chamber 828A–828N corresponding to each separation column 818A–818N. Preferably, each storage region 828A–828N is microfluidic. Each storage region 828A–828N may have a predetermined fixed volume or a variable volume. Variable volume storage chambers elements 828A–828N may include, for example, expandable bladders, collapsible portions, or moveable pistons (not shown). Each storage chamber 818A–828N preferably has one associated upstream purge valve 825A–825N and one downstream purge valve 829A–829N, with each valve 825A–825N, 829A–829N preferably being independently actuatable. Preferably, the upstream purge valves 825A–825N are multi-position valves to enable connections between different fluidic conduits depending on the valve position.

During eluate collection or storage, the upstream purge valves 825A–825N and downstream purge valves 829A–829N are preferably closed. When it is desired to purge the eluate contents of one storage chamber (e.g., chamber 828A), its associated downstream purge (e.g., valve 829A) is opened and its associated upstream purge valve (e.g., valve 825A) is switched into a position to permit fluid communication between an upstream pressure source 827 and the storage chamber (e.g., storage chamber 828A). Optionally, the upstream purge valve may also temporarily establish a fluidic path between the outlet of the column (e.g., column 818A) and a waste reservoir 821 to minimize pressure build-up within the column (e.g., column 818A). Upon establishment of a fluid path between the upstream pressure source 827 and the storage chamber (e.g., storage chamber 828A), the eluate contents of the storage chamber are purged through the associated downstream purge valve (e.g., valve 829A) in the direction of a downstream mass spectrometer 839 having an associated mass analyzer (not shown).

Further valves or junctions 830A–830N may be provided to permit the injection of a supplementing liquid by way of a supplementing liquid source 842. If electrospray ionization is used, then a substantially uninterrupted flow of supplementing liquid helps to maintain uninterrupted electrospray plumes from each electrospray ionization source—despite only periodic addition of eluate fractions—thus preventing undesirable sputtering or electrospray initiation delays. The supplementing liquid, if used, may be any liquid suitable for the particular ionization mechanism.

Sensors 831A–831N may be further disposed between the storage elements 828A–828N and the ionization element(s) 833. Preferred sensor types include flow and pressure sensors. Such sensors may be used to assist with ionization, such as by providing feedback signals to an energy source 832 associated with the ionization element(s) 833, or by providing feedback or feed-forward signals to pressure regulation elements (not shown) disposed upstream of the ionization element(s) 833. Alternatively, such sensors may be used to assist with directing ionized fractions within a downstream manifold 835, such as by providing feedback or feed-forward signals to means for directing the ionized discrete fraction of each eluate stream within the manifold 835. Examples of such directing means include a pressure source 835 (e.g., for supplying pressurized gas to the manifold 835) or ion optics 841A–841× disposed within the manifold 835.

Two alternative system configurations are shown to provide ionization utility, depending on whether it is desired to collect analyte-containing eluate as a liquid for subsequent ionization through a common ionization element 836, or (more preferably) whether it is instead desired to ionize analytes from the eluate first and then collect the ions in a manifold 835 preferably containing a flow of carrier gas (via pressure source 833) to direct the ions into a mass spectrometer 839. In the former configuration, a source of nebulizing gas 833 may be substituted for the upstream ionization elements 830 with ionization performed with the downstream ionization element(s) 836 (e.g., by photoionization or atmospheric pressure chemical ionization), while the latter configuration would preferably utilize multiple upstream ionization elements 833 but omit the downstream ionization element 836 and associated energy source 837. In either configuration, it is preferable to supply sufficient purge fluid (e.g., gas or liquid) flow from the first pressure source 827 and/or the second pressure source 834 to accomplish flushing of the eluate storage elements 828A–828N, ionization elements (830 or 836), and manifold 835 so as to minimize sample contamination or carryover problems.

In operation of the system 800, samples are provided to the columns 818A–818N and separated in parallel. A discrete fraction of eluate from each separation column 818A–818N is collected and stored in a different storage element 828A–828N in parallel. Each discrete fraction may have a volume substantially equal to the volume of its corresponding storage chamber 828A–828N. A first discrete fraction of eluate is purged from a first storage element (e.g., chamber 828A) by operating an upstream purge valve (e.g., valve 825A) and downstream purge valve (e.g., valve 826A) while a pressurized purge fluid is supplied through the chamber 828 by way of a pressure source 827 in the direction of a mass spectrometer 839. The purge fluid supplied by the pressure source 827 may be either liquid or gas. If liquid purge fluid is used, then each eluate/purge fluid pulse may flow as a liquid into a manifold and then later be ionized within a downstream ionization element 836. Alternatively, if gaseous purge fluid is used, then each eluate/purge fluid pulse may flow into ionization elements 830 disposed upstream of a collection manifold 835 that directs ionized analytes into the inlet of a mass spectrometer with assistance of gas flow provided by an additional pressure source 833. Each storage chamber 828 is purged and its contents ionized in sequence to yield a composite ion stream in the manifold 835 that is subsequently analyzed by the mass spectrometer 839. The composite ion stream includes a series of ionized discrete fractions of each eluate stream; i.e., one ionized discrete fraction of a first eluate stream received from a first storage chamber 828A followed by a another ionized discrete fraction of a second eluate stream received from a second storage chamber 828B, and so on. Following the sequential discharge and ionization of eluate fractions from each storage chamber 828A–828N, the cycle is continued until a first cycle is complete, at which point another cycle is initiated, and so on. In a preferred embodiment, each storage chamber 828A–828N is contained within a rotary storage device such as the devices 730, 760 described previously or the device 901 to be described hereinafter.

While the manifold 835 illustrated in FIG. 9 is shown as being orthogonal to the storage elements 828A–828N and upstream ionization elements 833, any appropriate relative configuration between the manifold 835, ionization elements 833/836, and the mass spectrometer 839 may be provided. If it is desired to direct ions within the manifold 835 with electrical or magnetic fields, then ion optics 841A–841X may be disposed within the manifold 835. Alternatively, pressure differentials may be used to manipulate the trajectory of ions within the manifold 835, such as by supplying pressurized gas by way of the pressure source 834. If pressurized carrier gas is supplied to the manifold by way of the pressure source 834, then compared to the aggregate flow rate of the various previously stored eluate streams to the manifold 835, the carrier gas has a flow rate of preferably at least about two times the aggregate eluate flow, more preferably at least about five time the aggregate eluate flow, and more preferably still at least about ten times the aggregate eluate flow. It is believed the such flows help reduce cross-talk between different eluate streams and adequately flush the manifold between injections of eluate fractions.

The system 800 illustrated in FIG. 9 supports the performance of various high throughput analytical methods. A preferred high throughput analytical method includes several method steps. A first method step includes separating multiple samples in parallel utilizing a multiple liquid phase separation process regions 818A–818N to yield multiple eluate streams. A second method step includes storing a discrete fraction of each eluate stream in parallel in multiple (e.g., microfluidic) storage regions 828A–828N. A third method step includes sequentially discharging and ionizing (e.g., using ionization source(s) 833) the discrete fraction of each eluate stream to yield a composite ion stream comprising a series of ionized discrete fractions of each eluate stream. A fourth method step includes analyzing the composite ion stream using a single mass spectrometer 839. If a manifold 835 is provided between the ionization source(s) 833 and the mass spectrometer 839, then another step may include directing the ionized discrete fraction of each eluate stream within the manifold 835 toward the mass spectrometer inlet, such as by supplying a stream of pressurized gas to the manifold 835 or by generating electric or magnetic fields within the manifold 835. Another method step may include supplying a supplementing liquid (e.g., from a supplementing liquid source 842) to each ionization source 833. Yet another method step may include sensing any of flow rate and pressure (e.g., using sensors 831A–831N) of the discrete fraction of each eluate stream prior to the ionizing step. Ionization and/or directing of ionized fractions within the manifold 835 may be responsive to the sensing step.

Briefly, the system 800 permits parallel separation and parallel storage of discrete eluate fractions, followed by sequential discharge and ionization of previously stored eluate portions to yield a composite ion stream containing the sequential series of eluate portions, followed by mass analysis of the ion stream. This hybrid parallel/serial system with low-capacity eluate storage provides rapid operation without any loss of eluate, thus ensuring the integrity of the analytical data obtained from the system.

In a preferred method in which the separating step includes the generation of a (e.g., absorbance) chromatogram for each separated sample, each chromatogram includes at least one sample component peak. Each sample component peak has a full-width/half-maximum peak duration, such that one peak of the aggregate group has a minimum peak duration. To promote adequate mass analysis data resolution, the sequential discharge and ionization step of the eluate fraction in each storage region is preferably performed at least about three times within the minimum full-width/half maximum peak duration; is more preferably performed at least about five times within the minimum full-width/half maximum peak duration; and is more preferably still performed at least about ten times within the minimum full-width/half maximum peak duration.

HPLC/MS Interface Usinq Loop-Type Rotary Storage Valves

In certain embodiments, loop-type rotary storage valves, preferably providing multiple fluid paths, may be utilized within a multi-column HPLC/MS interface system. Rotary-type sample injection valves are commonly utilized for loading samples into HPLC columns. In this application, however, multi-path loop valves are applied downstream of separation columns to receive eluate and facilitate its introduction to a mass spectrometer. A schematic of a first loop-type multi-path rotary storage valve 901 in a first state of operation is shown in FIG. 10A. The valve 901 includes a first eluate storage loop 902 and a second waste loop 904. FIG. 10A illustrates the valve 901 in a loading state. The first eluate storage loop 902 is disposed in a position to establish a fluidic path between the outlet of a separation column 918 and a waste reservoir 922. Despite the appearance of this fluidic connection, the intent is not to divert a significant amount of eluate to waste; rather, the intent is to reduce backpressure within the loop 902 and to meter a repeatable sample volume by filling the first loop 902 completely with eluate just until the leading edge of advancing eluate is about to be directed to the waste reservoir 922. One or more sensors (not shown) may be provided to sense the readiness of the valve 901 (e.g., by monitoring the presence or position of the advancing eluate front) to be switched to a second operating state. Notable, with the valve 901 in the first operating state, a second fluidic path between a low pressure source 927 and another waste reservoir 921 is established to flush any former contents of second waste loop 904 to waste by fluid (preferably gas) supplied from a low pressure source 927.

The interior portion of the valve 901 including both sample loops 902, 904 may be rotated (in the present case by 45 degrees in a counter-clockwise direction) to establish two different fluid paths through the valve 901. The second waste loop 904 establishes a pathway between the outlet of a separation column 918 and a waste reservoir 921. Establishment of this pathway prevents undue elevation of backpressure within the separation column 918. At the same time, the first eluate storage loop 902—now containing a plug of eluate defined by the volume of the loop 902—is disposed between a high pressure source 933 and the inlet of a mass spectrometer 939. Fluid (preferably gas) from the high pressure source 933 pushes the plug of eluate defined in the first loop 902 out of the valve 901 and toward the mass spectrometer. The valve can then be returned to its first operating state.

Multiple loop-type valves 901 may be provided within a multi-column HPLC/MS interface system. Each valve 901 may be actuated with conventional actuating components such as one or more of: a motor, a stepper motor, a solenoid, a piston, a cam/follower, and a four-bar mechanism. The rotary portion of each valve 901 may move at a constant angular velocity, or in an accelerated start-stop fashion to minimize the delay time between the purge of each different chamber.

Thus, various inventive systems and elements thereof have been described herein. It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention as defined by the appended claims and their equivalents.

What is claimed is:

1. A high throughput analytical system comprising:
a plurality of liquid phase separation process regions adapted to operate in parallel;
a rotary storage device comprising a plurality of storage chambers, each storage chamber of the plurality of storage chambers being associated with and being in at least intermittent fluid communication with a different liquid phase separation process region of the plurality of liquid phase separation process regions;
a plurality of ionization sources disposed downstream of and in at least intermittent fluid communication with the plurality of storage chambers;
a mass spectrometer having a mass analyzer and an inlet in at least intermittent fluid communication with the plurality of ionization sources.

2. The system of claim 1 wherein the rotary storage device comprises a common actuator.

3. The system of claim 1 wherein the rotary storage device comprises a stationary portion and a rotating portion.

4. The system of claim 1 wherein each storage chamber of the plurality of storage chambers is microfluidic.

5. The system of claim 1, further comprising a manifold disposed between the plurality of ionization sources and the mass spectrometer inlet.

6. The system of claim 5, further comprising ion optics disposed within the manifold.

7. The system of claim 5, further comprising a supply of pressurized carrier gas in at least intermittent fluid communication with the manifold.

8. The system of claim 1, further comprising a supply of supplementing liquid in at least intermittent fluid communication with the plurality of ionization sources.

9. The system of claim 8 wherein each ionization source of the plurality of ionization sources operates in a substantially continuous manner.

10. The system of claim 1, further comprising a plurality of sensors disposed between the plurality of storage chambers and the plurality of ionization elements.

11. The system of claim 10 wherein the plurality of sensors comprises any of flow sensors and pressure sensors.

12. The system of claim 1, further comprising a supply of pressurized gas in intermittent fluid communication with each storage chamber of the plurality of storage chambers.

13. The system of claim 1 wherein the mass spectrometer comprises a time of flight mass spectrometer.

14. The system of claim 1 wherein the plurality of liquid phase separation process regions comprises at least ten liquid phase separation process regions.

15. The system of claim 1 wherein each liquid phase separation process region of the plurality of liquid phase separation process regions comprises a chromatography column.

16. The system of claim 1, further comprising a common source of mobile phase, wherein each liquid phase separation process region of the plurality of liquid phase separation process regions is in fluid communication with the common source of mobile phase.

17. The system of claim 1 wherein each ionization source of the plurality of ionization sources comprises an electrospray ionization source.

18. The system of claim 1 wherein each storage chamber has a fixed volume.

19. A high throughput analytical method comprising the steps of:
separating a plurality of samples in parallel utilizing a plurality of liquid phase separation process regions to yield a plurality of eluate streams;
storing a discrete fraction of each eluate stream of the plurality of eluate streams in parallel in a plurality of microfluidic storage regions; and
sequentially discharging and ionizing the discrete fraction of each eluate stream of the plurality of eluate streams to yield a composite ion stream comprising a series of ionized discrete fractions of each eluate stream of the plurality of eluate streams; and
analyzing the composite ion stream using a single mass spectrometer.

20. The method of claim 19, further comprising the steps of:
providing a plurality of ionization sources in at least intermittent fluid communication with the plurality of storage regions;
providing a manifold disposed between the plurality of ionization sources and the mass spectrometer; and
directing the ionized discrete fraction of each eluate stream within the manifold toward the mass spectrometer inlet.

21. The method of claim 20 wherein the directing step includes supplying a stream of pressurized gas to the manifold.

22. The method of claim 20 wherein the directing step includes generating at least one of an electric field and a magnetic field within the manifold.

23. The method of claim 19, further comprising the steps of:
providing a plurality of ionization sources in at least intermittent fluid communication with the plurality of storage regions; and
supplying a supplementing liquid to each ionization source of the plurality of ionization sources.

24. The method of claim 23 wherein the supplemental liquid supplying step is substantially uninterrupted during the sequential discharging step.

25. The method of claim 19, further comprising the step of sensing any of flow rate and pressure of the discrete fraction of each eluate stream of the plurality of eluate streams prior to the ionizing step.

26. The method of claim 25, wherein the ionizing step is responsive to the sensing step.

27. The method of claim 25, further comprising the steps of:
providing a plurality of ionization sources in at least intermittent fluid communication with the plurality of storage regions;
providing a manifold disposed between the plurality of ionization sources and the mass spectrometer; and
sequentially directing the ionized discrete fraction of each eluate stream within the manifold toward the mass spectrometer inlet, wherein the directing step is responsive to the sensing step.

28. The method of claim 19 wherein the sequential discharging step includes purging each storage region with a pressurized gas.

29. The method of claim 19, further comprising the step of detecting a property of each eluate stream of the plurality of eluate streams after the separating step, wherein the storing step is responsive to the detecting step.

30. The method of claim 19 wherein each liquid phase separation process region of the plurality of liquid phase separation process regions comprises a chromatography column, and the separating step includes performing a chromatographic separation process within each liquid phase separation process region of the plurality of liquid phase separation process regions.

31. The method of claim 19 wherein the plurality of microfluidic storage regions is disposed within a rotary device having a common actuator.

32. The method of claim 19 wherein the mass spectrometer comprises a time of flight mass spectrometer.

33. The method of claim 19 wherein each microfluidic storage region has a fixed first volume, and the discrete fraction of each eluate stream of the plurality of eluate streams has a volume substantially equal to the fixed first volume.

34. The method of claim 19 wherein the sequential discharge step includes discharging each microfluidic storage region of the plurality of microfluidic storage regions at least about once per second.

35. The method of claim 19 wherein the sequential discharge step includes discharging each microfluidic storage region of the plurality of microfluidic storage regions at least about twice per second.

36. The method of claim 19 wherein the sequential discharge step includes discharging each microfluidic storage region of the plurality of microfluidic storage regions at least about five times per second.

37. The method of claim 21 wherein the pressurized carrier gas is supplied to the manifold at a first flow rate, the previously stored eluate stream portions are supplied to the manifold at an aggregated second flow rate, and the first flow rate is at least about two times greater than the first flow rate.

38. The method of claim 21 wherein the pressurized carrier gas is supplied to the manifold at a first flow rate, the previously stored eluate stream portions are supplied to the manifold at an aggregated second flow rate, and the first flow rate is at least about five times greater than the first flow rate.

39. The method of claim 21 wherein the pressurized carrier gas is supplied to the manifold at a first flow rate, the previously stored eluate stream portions are supplied to the manifold at an aggregated second flow rate, and the first flow rate is at least about ten times greater than the first flow rate.

40. The method of claim 19 wherein:
the separating step includes generating a plurality of chromatograms for the plurality of samples;
each chromatogram of the plurality of chromatograms includes at least one sample component peak, with the plurality of chromatograms in the aggregate including a plurality of sample component peaks;
each sample component peak of the plurality of sample component peaks has a full-width/half-maximum peak duration;
the plurality of sample component peaks includes a peak having a minimum full-width/half-maximum peak duration; and
the sequential discharging and ionizing step is performed at least about three times within the minimum full-width/half maximum peak duration.

41. The method of claim 19 wherein:
the separating step includes generating a plurality of chromatograms for the plurality of samples;
each chromatogram of the plurality of chromatograms includes at least one sample component peak, with the plurality of chromatograms in the aggregate including a plurality of sample component peaks;
each sample component peak of the plurality of sample component peaks has a full-width/half-maximum peak duration;
the plurality of sample component peaks includes a peak having a minimum full-width/half-maximum peak duration; and
the sequential discharging and ionizing step is performed at least about five times within the minimum full-width/half maximum peak duration.

42. The method of claim 19 wherein:
the separating step includes generating a plurality of chromatograms for the plurality of samples;
each chromatogram of the plurality of chromatograms includes at least one sample component peak, with the plurality of chromatograms in the aggregate including a plurality of sample component peaks;
each sample component peak of the plurality of sample component peaks has a full-width/half-maximum peak duration;
the plurality of sample component peaks includes a peak having a minimum full-width/half-maximum peak duration; and
the sequential discharging and ionizing step is performed at least about ten times within the minimum full-width/half maximum peak duration.

43. A high throughput analytical method comprising the steps of:
providing a plurality of liquid phase separation process regions;
providing a plurality of microfluidic storage regions, each storage region being associated with and in at least intermittent fluid communication with a different liquid phase separation process region of the plurality of liquid phase separation process regions;
providing a plurality of ionization sources in intermittent fluid communication with the plurality of microfluidic storage regions;
providing a mass spectrometer having an inlet and having an associated manifold in at least intermittent fluid communication with the plurality of ionization sources;
supplying a plurality of samples to the plurality of liquid phase separation process regions;
separating the plurality of samples in parallel in the plurality of liquid phase separation process regions to yield a plurality of eluate streams;
storing a discrete fraction of each eluate stream of the plurality of eluate streams in parallel in a different microfluidic storage region of the plurality of microfluidic storage regions;
sequentially discharging and ionizing the discrete fraction of each eluate stream of the plurality of eluate streams into the manifold to yield a composite ion stream comprising a series of ionized discrete fractions of each eluate stream of the plurality of eluate streams; and
analyzing the composite ion stream using the mass spectrometer.

44. The method of claim 43, further comprising the step of supplying a stream of pressurized carrier gas to the manifold.

45. The method of claim 43, further comprising the step of sequentially directing the ionized discrete fraction of each eluate stream within the manifold toward the mass spectrometer inlet utilizing at least one of an electric field and a magnetic field.

46. The method of claim 43, further comprising the step of supplying a supplementing liquid to each ionization source of the plurality of ionization sources.

47. The method of claim 46 wherein the supplemental liquid supplying step is substantially uninterrupted during the sequential discharging step.

48. The method of claim 43, further comprising the step of sensing any of flow rate and pressure of the discrete fraction of each eluate stream of the plurality of eluate streams prior to the ionizing step.

49. The method of claim 48, wherein the ionizing step is responsive to the sensing step.

50. The method of claim 48, further comprising the step of sequentially directing the ionized discrete fraction of each eluate stream within the manifold toward the mass spectrometer inlet responsive to the sensing step.

51. The method of claim 43 wherein the sequential discharging step includes purging each storage region with a pressurized gas.

52. The method of claim 43, further comprising the step of detecting a property of each eluate stream of the plurality of eluate streams after the separating step, wherein the storing step is responsive to the detecting step.

53. The method of claim 43 wherein each liquid phase separation process region of the plurality of liquid phase separation process regions comprises a chromatography column, and the separating step includes performing a chromatographic separation process within each liquid phase separation process region of the plurality of liquid phase separation process regions.

54. The method of claim 43 wherein the plurality of microfluidic storage regions is disposed within a rotary device having a common actuator.

55. The method of claim 43 wherein the mass spectrometer comprises a time of flight mass spectrometer.

56. The method of claim 43 wherein each microfluidic storage region has a fixed first volume, and the discrete fraction of each eluate stream of the plurality of eluate streams has a volume substantially equal to the fixed first volume.

57. The method of claim 43 wherein the sequential discharge step includes discharging each microfluidic storage region of the plurality of microfluidic storage regions at least about once per second.

58. The method of claim 43 wherein the sequential discharge step includes discharging each microfluidic storage region of the plurality of microfluidic storage regions at least about twice per second.

59. The method of claim 43 wherein the sequential discharge step includes discharging each microfluidic storage region of the plurality of microfluidic storage regions at least about five times per second.

60. The method of claim 44 wherein the pressurized carrier gas is supplied to the manifold at a first flow rate, the previously stored eluate stream portions are supplied to the manifold at an aggregated second flow rate, and the first flow rate is at least about two times greater than the first flow rate.

61. The method of claim 44 wherein the pressurized carrier gas is supplied to the manifold at a first flow rate, the previously stored eluate stream portions are supplied to the manifold at an aggregated second flow rate, and the first flow rate is at least about five times greater than the first flow rate.

62. The method of claim 44 wherein the pressurized carrier gas is supplied to the manifold at a first flow rate, the previously stored eluate stream portions are supplied to the manifold at an aggregated second flow rate, and the first flow rate is at least about ten times greater than the first flow rate.

63. The method of claim 43 wherein:
the separating step includes generating a plurality of chromatograms for the plurality of samples;
each chromatogram of the plurality of chromatograms includes at least one sample component peak, with the plurality of chromatograms in the aggregate including a plurality of sample component peaks;
each sample component peak of the plurality of sample component peaks has a full-width/half-maximum peak duration;
the plurality of sample component peaks includes a peak having a minimum full-width/half-maximum peak duration; and
the sequential discharging and ionizing step is performed at least about three times within the minimum full-width/half maximum peak duration.

64. The method of claim 43 wherein:
the separating step includes generating a plurality of chromatograms for the plurality of samples;
each chromatogram of the plurality of chromatograms includes at least one sample component peak, with the plurality of chromatograms in the aggregate including a plurality of sample component peaks;
each sample component peak of the plurality of sample component peaks has a full-width/half-maximum peak duration;
the plurality of sample component peaks includes a peak having a minimum full-width/half-maximum peak duration; and
the sequential discharging and ionizing step is performed at least about five times within the minimum full-width/half maximum.

65. The method of claim 43 wherein:
the separating step includes generating a plurality of chromatograms for the plurality of samples;
each chromatogram of the plurality of chromatograms includes at least one sample component peak, with the plurality of chromatograms in the aggregate including a plurality of sample component peaks;
each sample component peak of the plurality of sample component peaks has a full-width/half-maximum peak duration;
the plurality of sample component peaks includes a peak having a minimum full-width/half-maximum peak duration; and
the sequential discharging and ionizing step is performed at least about ten times within the minimum full-width/half maximum peak duration.

* * * * *

UNITED STATES PATENT AND TRADEMARK OFFICE
CERTIFICATE OF CORRECTION

PATENT NO.        : 7,132,650 B1                                Page 1 of 1
APPLICATION NO. : 10/951255
DATED             : November 7, 2006
INVENTOR(S)       : Ronald C. Gamble et al.

It is certified that error appears in the above-identified patent and that said Letters Patent is hereby corrected as shown below:

In column 24, line 4, "ion optics 841A-841xdisposed" should be -- ion optics 841A-841X disposed --.

Signed and Sealed this

Sixth Day of February, 2007

JON W. DUDAS
*Director of the United States Patent and Trademark Office*